United States Patent
Carlson

(10) Patent No.: US 9,549,747 B2
(45) Date of Patent: Jan. 24, 2017

(54) REUSABLE SURGICAL RETRIEVAL APPARATUS WITH DISPOSABLE CARTRIDGE ASSEMBLY

(71) Applicant: Covidien LP, Mansfield, MA (US)

(72) Inventor: Erik Carlson, Meriden, CT (US)

(73) Assignee: COVIDIEN LP, Mansfield, MA (US)

( * ) Notice: Subject to any disclaimer, the term of this patent is extended or adjusted under 35 U.S.C. 154(b) by 268 days.

(21) Appl. No.: 13/713,075

(22) Filed: Dec. 13, 2012

(65) Prior Publication Data

US 2013/0190773 A1 Jul. 25, 2013

Related U.S. Application Data

(60) Provisional application No. 61/589,464, filed on Jan. 23, 2012.

(51) Int. Cl.
*A61B 17/24* (2006.01)
*A61B 17/26* (2006.01)
(Continued)

(52) U.S. Cl.
CPC ....... *A61B 17/221* (2013.01); *A61B 17/00234* (2013.01); *A61B 17/3421* (2013.01);
(Continued)

(58) Field of Classification Search
CPC ............ A61B 17/221; A61B 17/00234; A61B 17/3421; A61B 17/07207; A61B 17/068; A61B 17/00; A61B 2017/00287; A61B 2017/00477; A61B 2017/00473; A61B 2002/0072; A61F 2002/2484; A61F 2/0063; A61F 2/2481; A61F 2220/0016; A61L 31/145; A61M 1/008; Y10S 128/24
(Continued)

(56) References Cited

U.S. PATENT DOCUMENTS 30,471 A 10/1860 Dudley
35,164 A 5/1862 Logan et al.
(Continued)

FOREIGN PATENT DOCUMENTS

DE 3542667 A1 6/1986
DE 8435489 U1 8/1986
(Continued)

OTHER PUBLICATIONS

EP Search Report for EP 12158873 mailed Jul. 19, 2012.
Partial European Search Report EP 12 19 8768 dated Aug. 27, 2014.

*Primary Examiner* — Katherine M Shi
*Assistant Examiner* — Mohamed Gabr

(57) ABSTRACT

A surgical retrieval apparatus includes a tube assembly, a cartridge assembly, and a plunger assembly. The cartridge assembly is releasably engagable with the tube assembly and includes an end effector assembly disposed therein. The end effector assembly includes a specimen retrieval bag releasably coupled thereto at a distal end thereof and a first engagement member disposed at a proximal end thereof. The plunger assembly is configured for insertion through the tube assembly and into the cartridge assembly. The plunger assembly includes a second engagement member configured for releasably engaging the first engagement member. When the first and second engagement members are engaged with one another, the plunger assembly is movable between a more proximal position, wherein the end effector assembly and specimen retrieval bag are retracted within the cartridge assembly, and a more distal position, wherein the end effector assembly and specimen retrieval bag are deployed from the cartridge assembly.

18 Claims, 18 Drawing Sheets

(51) Int. Cl.
*A61B 17/221* (2006.01)
*A61B 17/00* (2006.01)
*A61B 17/34* (2006.01)

(52) U.S. Cl.
CPC ............ *A61B 2017/00287* (2013.01); *A61B 2017/00477* (2013.01)

(58) Field of Classification Search
USPC .......... 606/110, 113, 114, 127, 128; 604/27, 604/171, 317
See application file for complete search history.

(56) References Cited

U.S. PATENT DOCUMENTS

| | | | |
|---|---|---|---|
| 1,156,477 A | 11/1874 | Bradford | |
| 1,609,014 A | 11/1926 | Dowd | |
| 3,800,781 A | 4/1974 | Zalucki | |
| 4,557,255 A | 12/1985 | Goodman | |
| 4,611,594 A | 9/1986 | Grayhack et al. | |
| 4,744,363 A | 5/1988 | Hasson | |
| 4,790,812 A | 12/1988 | Hawkins, Jr. et al. | |
| 4,927,427 A | 5/1990 | Kriauciunas et al. | |
| 4,997,435 A | 3/1991 | Demeter | |
| 5,037,379 A | 8/1991 | Clayman et al. | |
| 5,074,867 A | 12/1991 | Wilk | |
| 5,084,054 A | 1/1992 | Bencini et al. | |
| 5,143,082 A | 9/1992 | Kindberg et al. | |
| 5,147,371 A | 9/1992 | Washington et al. | |
| 5,176,687 A | 1/1993 | Hasson et al. | |
| 5,190,542 A | 3/1993 | Nakao et al. | |
| 5,190,555 A | 3/1993 | Wetter et al. | |
| 5,190,561 A | 3/1993 | Graber | |
| 5,192,286 A | 3/1993 | Phan et al. | |
| 5,201,740 A | 4/1993 | Nakao et al. | |
| 5,215,521 A | 6/1993 | Cochran et al. | |
| 5,224,930 A | 7/1993 | Spaeth et al. | |
| 5,234,439 A | 8/1993 | Wilk et al. | |
| 5,279,539 A | 1/1994 | Bohan et al. | |
| 5,312,416 A | 5/1994 | Spaeth et al. | |
| 5,330,483 A | 7/1994 | Heaven et al. | |
| 5,336,227 A | 8/1994 | Nakao et al. | |
| 5,337,754 A | 8/1994 | Heaven et al. | |
| 5,341,815 A | 8/1994 | Cofone et al. | |
| 5,352,184 A | 10/1994 | Goldberg et al. | |
| 5,352,219 A | 10/1994 | Reddy | |
| 5,354,303 A | 10/1994 | Spaeth et al. | |
| 5,368,545 A | 11/1994 | Schaller et al. | |
| 5,368,597 A | 11/1994 | Pagedas | |
| 5,370,647 A | 12/1994 | Graber et al. | |
| 5,465,731 A * | 11/1995 | Bell ................ | A61B 17/00234 600/37 |
| 5,480,404 A | 1/1996 | Kammerer et al. | |
| 5,486,182 A | 1/1996 | Nakao et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,535,759 A | 7/1996 | Wilk | |
| 5,611,803 A | 3/1997 | Heaven et al. | |
| 5,618,296 A | 4/1997 | Sorensen et al. | |
| 5,630,822 A | 5/1997 | Hermann et al. | |
| 5,642,282 A | 6/1997 | Sonehara | |
| 5,643,282 A | 7/1997 | Kieturakis | |
| 5,643,283 A | 7/1997 | Younker | |
| 5,645,083 A | 7/1997 | Essig et al. | |
| 5,647,372 A | 7/1997 | Tovey et al. | |
| 5,649,902 A | 7/1997 | Yoon | |
| 5,658,296 A | 8/1997 | Bates et al. | |
| 5,679,423 A | 10/1997 | Shah | |
| 5,735,289 A | 4/1998 | Pfeffer et al. | |
| 5,755,724 A | 5/1998 | Yoon | |
| 5,759,187 A | 6/1998 | Nakao et al. | |
| 5,769,794 A | 6/1998 | Conlan et al. | |
| 5,785,677 A | 7/1998 | Auweiler | |
| 5,788,709 A | 8/1998 | Riek et al. | |
| 5,792,145 A | 8/1998 | Bates et al. | |
| 5,814,044 A | 9/1998 | Hooven | |
| 5,836,953 A | 11/1998 | Yoon | |
| 5,853,374 A | 12/1998 | Hart et al. | |
| 5,895,392 A | 4/1999 | Riek et al. | |
| 5,906,621 A | 5/1999 | Secrest et al. | |
| 5,957,884 A | 9/1999 | Hooven | |
| 5,971,995 A | 10/1999 | Rousseau | |
| 5,980,544 A | 11/1999 | Vaitekunas | |
| 5,997,547 A | 12/1999 | Nakao et al. | |
| 6,004,330 A | 12/1999 | Middleman et al. | |
| 6,007,512 A | 12/1999 | Hooven | |
| 6,019,770 A | 2/2000 | Christoudias | |
| 6,036,681 A | 3/2000 | Hooven | |
| 6,059,793 A * | 5/2000 | Pagedas ........... | A61B 17/00234 128/DIG. 24 |
| 6,123,701 A | 9/2000 | Nezhat | |
| 6,152,932 A | 11/2000 | Ternstrom | |
| 6,162,235 A | 12/2000 | Vaitekunas | |
| 6,165,121 A | 12/2000 | Alferness | |
| 6,168,603 B1 | 1/2001 | Leslie et al. | |
| 6,228,095 B1 * | 5/2001 | Dennis ............. | A61B 17/00234 606/114 |
| 6,270,505 B1 | 8/2001 | Yoshida et al. | |
| 6,277,083 B1 | 8/2001 | Eggers et al. | |
| 6,280,450 B1 | 8/2001 | McGuckin, Jr. | |
| 6,344,026 B1 | 2/2002 | Burbank et al. | |
| 6,348,056 B1 | 2/2002 | Bates et al. | |
| 6,350,266 B1 | 2/2002 | White et al. | |
| 6,350,267 B1 * | 2/2002 | Stefanchik ....... | A61B 17/00234 606/114 |
| 6,383,195 B1 | 5/2002 | Richard | |
| 6,383,196 B1 | 5/2002 | Leslie et al. | |
| 6,383,197 B1 * | 5/2002 | Conlon ............ | A61B 17/00234 600/37 |
| 6,387,102 B2 * | 5/2002 | Pagedas ........... | A61B 17/00234 606/127 |
| 6,406,440 B1 * | 6/2002 | Stefanchik ....... | A61B 17/00234 600/562 |
| 6,409,733 B1 * | 6/2002 | Conlon ............ | A61B 17/00234 600/37 |
| 6,419,639 B2 | 7/2002 | Walther et al. | |
| 6,447,523 B1 | 9/2002 | Middleman et al. | |
| 6,471,659 B2 | 10/2002 | Eggers et al. | |
| 6,506,166 B1 | 1/2003 | Hendler et al. | |
| 6,508,773 B2 | 1/2003 | Burbank et al. | |
| 6,589,252 B2 | 7/2003 | McGuckin, Jr. | |
| 6,752,811 B2 | 6/2004 | Chu et al. | |
| 6,755,779 B2 * | 6/2004 | Vanden Hoek ....... | A61F 2/2481 128/898 |
| 6,780,193 B2 | 8/2004 | Leslie et al. | |
| 6,805,699 B2 | 10/2004 | Shimm | |
| 6,840,948 B2 | 1/2005 | Albrecht et al. | |
| 6,872,211 B2 | 3/2005 | White et al. | |
| 6,887,255 B2 | 5/2005 | Shimm | |
| 6,994,696 B2 | 2/2006 | Suga | |
| 7,052,454 B2 | 5/2006 | Taylor | |
| 7,052,501 B2 | 5/2006 | McGuckin, Jr. | |
| 7,090,637 B2 | 8/2006 | Danitz et al. | |
| 7,249,788 B2 * | 7/2007 | Muhammad et al. ........ 285/319 | |
| 7,270,663 B2 | 9/2007 | Nakao | |
| 7,273,488 B2 | 9/2007 | Nakamura et al. | |
| 7,410,491 B2 | 8/2008 | Hopkins et al. | |
| 7,547,310 B2 | 6/2009 | Whitfield | |
| 7,670,346 B2 * | 3/2010 | Whitfield .................... 606/114 | |
| 8,734,464 B2 * | 5/2014 | Grover ................. | A61B 17/00 606/114 |
| 9,241,715 B2 * | 1/2016 | Kasvikis .......... | A61B 17/07207 |
| 9,271,639 B2 * | 3/2016 | Cruz ................. | A61B 17/0218 |
| 2004/0097960 A1 | 5/2004 | Terachi et al. | |
| 2004/0138587 A1 | 7/2004 | Lyons | |
| 2005/0267492 A1 | 12/2005 | Poncet et al. | |
| 2006/0052799 A1 | 3/2006 | Middleman et al. | |
| 2006/0058776 A1 | 3/2006 | Bilsbury | |
| 2006/0200169 A1 * | 9/2006 | Sniffin ............. | A61B 17/00234 606/113 |
| 2006/0200170 A1 | 9/2006 | Aranyi | |

(56) References Cited

U.S. PATENT DOCUMENTS

| | | | |
|---|---|---|---|
| 2006/0229639 A1* | 10/2006 | Whitfield | A61B 17/00234 606/114 |
| 2006/0229640 A1* | 10/2006 | Whitfield | A61B 17/221 606/114 |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2008/0188766 A1 | 8/2008 | Gertner | |
| 2008/0221588 A1* | 9/2008 | Hollis | A61B 17/00234 606/114 |
| 2008/0234696 A1* | 9/2008 | Taylor | A61B 17/00234 606/114 |
| 2008/0300621 A1 | 12/2008 | Hopkins et al. | |
| 2008/0312496 A1 | 12/2008 | Zwolinski | |
| 2009/0082779 A1 | 3/2009 | Nakao | |
| 2009/0182292 A1* | 7/2009 | Egle | A61B 17/00234 604/327 |
| 2009/0192510 A1 | 7/2009 | Bahney | |
| 2009/0240238 A1 | 9/2009 | Grodrian et al. | |
| 2010/0000471 A1 | 1/2010 | Hibbard | |
| 2011/0184430 A1* | 7/2011 | Parihar | A61B 17/00234 606/114 |
| 2011/0184432 A1* | 7/2011 | Parihar | A61B 17/00234 606/114 |
| 2011/0184436 A1* | 7/2011 | Shelton, IV | A61B 17/00234 606/114 |
| 2011/0190781 A1 | 8/2011 | Collier et al. | |
| 2011/0299799 A1 | 12/2011 | Towe | |
| 2012/0083797 A1* | 4/2012 | Cabrera | A61B 17/00234 606/114 |
| 2012/0259347 A1* | 10/2012 | Abuzaina | A61B 17/00234 606/142 |
| 2013/0103043 A1* | 4/2013 | Cabrera | A61B 17/00234 606/114 |
| 2013/0209659 A1* | 8/2013 | Racenet | A61L 31/145 427/2.1 |
| 2014/0263555 A1* | 9/2014 | Hufnagel | A61B 17/068 227/176.1 |
| 2014/0371760 A1* | 12/2014 | Menn | A61B 17/00234 606/114 |
| 2015/0088169 A1* | 3/2015 | Kelly | A61F 2/0063 606/151 |
| 2015/0209035 A1* | 7/2015 | Zemlok | G01D 18/008 73/1.01 |

FOREIGN PATENT DOCUMENTS

| | | |
|---|---|---|
| DE | 4204210 A1 | 8/1992 |
| DE | 19624826 A1 | 1/1998 |
| EP | 2098170 A2 | 9/2009 |
| EP | 2184014 A2 | 5/2010 |
| FR | 1272412 A | 9/1961 |
| WO | 93/15671 A1 | 8/1993 |
| WO | 9315675 A1 | 8/1993 |
| WO | 9509666 A1 | 4/1995 |
| WO | 2004002334 A1 | 1/2004 |
| WO | 2004/112571 A2 | 12/2004 |
| WO | 2005/112783 A1 | 12/2005 |
| WO | 2011/090862 A2 | 7/2011 |

* cited by examiner

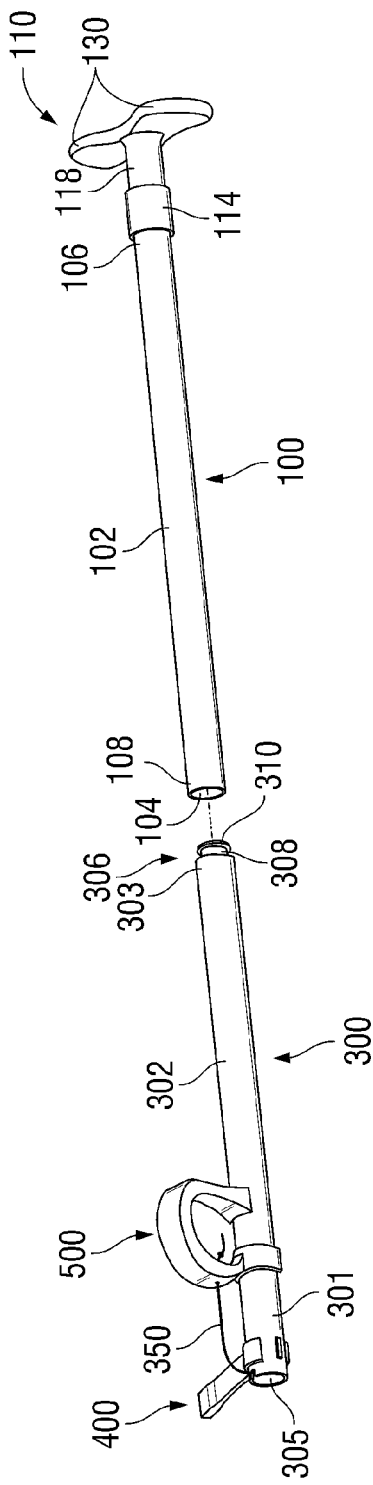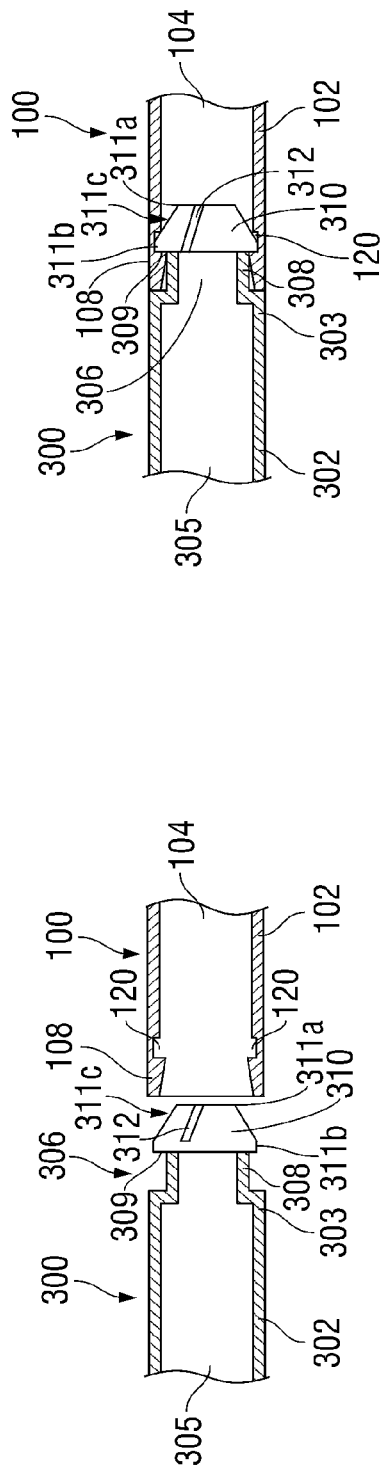
FIG. 6
FIG. 7A
FIG. 7B

REUSABLE SURGICAL RETRIEVAL APPARATUS WITH DISPOSABLE CARTRIDGE ASSEMBLY

CROSS-REFERENCE TO RELATED APPLICATIONS

This application claims the benefit of and priority to U.S. Provisional Patent Application No. 61/589,464, filed Jan. 23, 2012, the entire disclosure of which is incorporated by reference herein.

BACKGROUND

Technical Field

The present disclosure relates to a retrieval apparatus, and more particularly, to a surgical retrieval apparatus that includes reusable components and a disposable cartridge assembly.

Background of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, abdominal, laparoscopic, and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to inhibit seeding of cancer cells.

SUMMARY

In accordance with embodiments of the present disclosure, a surgical retrieval apparatus is provided. The surgical retrieval apparatus includes a tube assembly, a cartridge assembly, and a plunger assembly. The tube assembly includes a lumen extending longitudinally therethrough. The cartridge assembly is releasably engagable with the tube assembly and includes an end effector assembly operably coupled thereto. The end effector assembly includes a specimen retrieval bag releasably coupled thereto at a distal end thereof and a first engagement member disposed at a proximal end thereof. The plunger assembly is configured for insertion at least partially through the lumen of the tube assembly and into the cartridge assembly. The plunger assembly includes a second engagement member that is configured for releasably engaging the first engagement member of the end effector assembly. When the first and second engagement members are engaged with one another, the plunger assembly is movable relative to the tube assembly and the cartridge assembly between a more proximal position, wherein the end effector assembly and specimen retrieval bag are retracted within the cartridge assembly, and a more distal position, wherein the end effector assembly extends distally from the cartridge assembly to deploy the specimen retrieval bag.

In one embodiment, the tube assembly and the cartridge assembly are configured for snap-fit engagement with one another. In such an embodiment, an audible feedback signal is produced upon snap-fit engagement of the tube assembly and the cartridge assembly with one another to indicate to the user that the tube assembly and the cartridge assembly are engaged with one another.

In another embodiment, the first engagement member and the second engagement member are configured for snap-fit engagement with one another. In such an embodiment, an audible feedback signal is produced upon snap-fit engagement of the first engagement member and the second engagement member with one another to indicate to the user that the plunger assembly and the end effector assembly are engaged with one another.

In another embodiment, the plunger assembly is further movable relative to the tube assembly and the cartridge assembly to an eject position to disengage the cartridge assembly and the tube assembly from one another.

In yet another embodiment, a lock tab is releasably engagable with the cartridge assembly. The lock tab is configured to inhibit deployment of the specimen retrieval bag when the lock tab is engaged with the cartridge assembly.

In still another embodiment, a cinch cord is coupled to an open end of the specimen retrieval bag. The cinch cord is selectively tensionable to cinch closed the specimen retrieval bag. Further, a cord slot may be defined within the cartridge assembly. The cord slot is configured to receive the cinch cord therethrough to facilitate closing of the specimen retrieval bag upon tensioning of the cinch cord.

In yet another embodiment, a pull ring is coupled to the cinch cord. The pull ring is selectively movable relative to the end effector assembly to cinch closed the specimen retrieval bag. Further, the pull ring may be configured to be movable from an initial position, wherein the pull ring is disposed about the cartridge assembly, to a use position, wherein the pull ring is disposed about the tube assembly. From the use position, the pull ring may be removed from the tube assembly and pulled proximally to cinch closed the specimen retrieval bag.

In still another embodiment, the specimen retrieval bag includes a perforated section adjacent an open end thereof. The specimen retrieval bag is configured to tear along the perforated section as the specimen retrieval bag is cinched closed to disengage the specimen retrieval bag from the end effector assembly.

In still yet another embodiment, the tube assembly and the plunger assembly are formed as reusable components, while the cartridge assembly is formed as a disposable component.

A surgical kit is provided in accordance with another embodiment of the present disclosure and generally includes a reusable tube assembly, a reusable plunger assembly, and a plurality of disposable cartridge assemblies. The reusable tube assembly includes a lumen extending longitudinally therethrough. The reusable plunger assembly is insertable at least partially through the lumen of the tube assembly. Each of the disposable cartridge assemblies is releasably engagable with the tube assembly and includes an end effector assembly that is operably disposed therein. Each of the end effector assemblies includes a specimen retrieval bag that is deployable from the cartridge assembly upon movement of the end effector assembly from a retracted position to an extended position. Further, each end effector assembly is releasably engagable with the plunger assembly such that movement of the plunger assembly between a more proximal position and a more distal position moves the end effector assembly between the retracted position and the extended position.

In one embodiment, the plunger assembly is further movable from the more distal position to an eject position to disengage the cartridge assembly and the tube assembly from one another.

In another embodiment, the tube assembly and the plunger assembly are each formed from a durable, sterilizable material to facilitate sterilization and reuse of the tube assembly and the plunger assembly.

In yet another embodiment, feedback, e.g., audible and/or tactile feedback, is provided upon engagement of the tube assembly and each of the cartridge assemblies with one another. Feedback, e.g., audible and/or tactile feedback, may also be provided upon engagement of the plunger assembly and each of the end effector assemblies with one another.

In another embodiment, each of the cartridge assemblies includes a lock tab releasably engagable therewith. The lock tab is configured to inhibit deployment of the specimen retrieval bag when the lock tab is engaged with the cartridge assembly.

BRIEF DESCRIPTION OF THE DRAWINGS

Various embodiments of the subject surgical retrieval apparatus are described herein with reference to the drawings wherein:

FIG. 6 is a perspective view of the cartridge assembly and the tube assembly disengaged from one another;

FIG. 7A is a longitudinal, cross-sectional view of the cartridge assembly and the tube assembly disengaged from one another;

FIG. 7B is a longitudinal, cross-sectional view of the cartridge assembly and the tube assembly engaged with one another;

DETAILED DESCRIPTION

Figure 1:
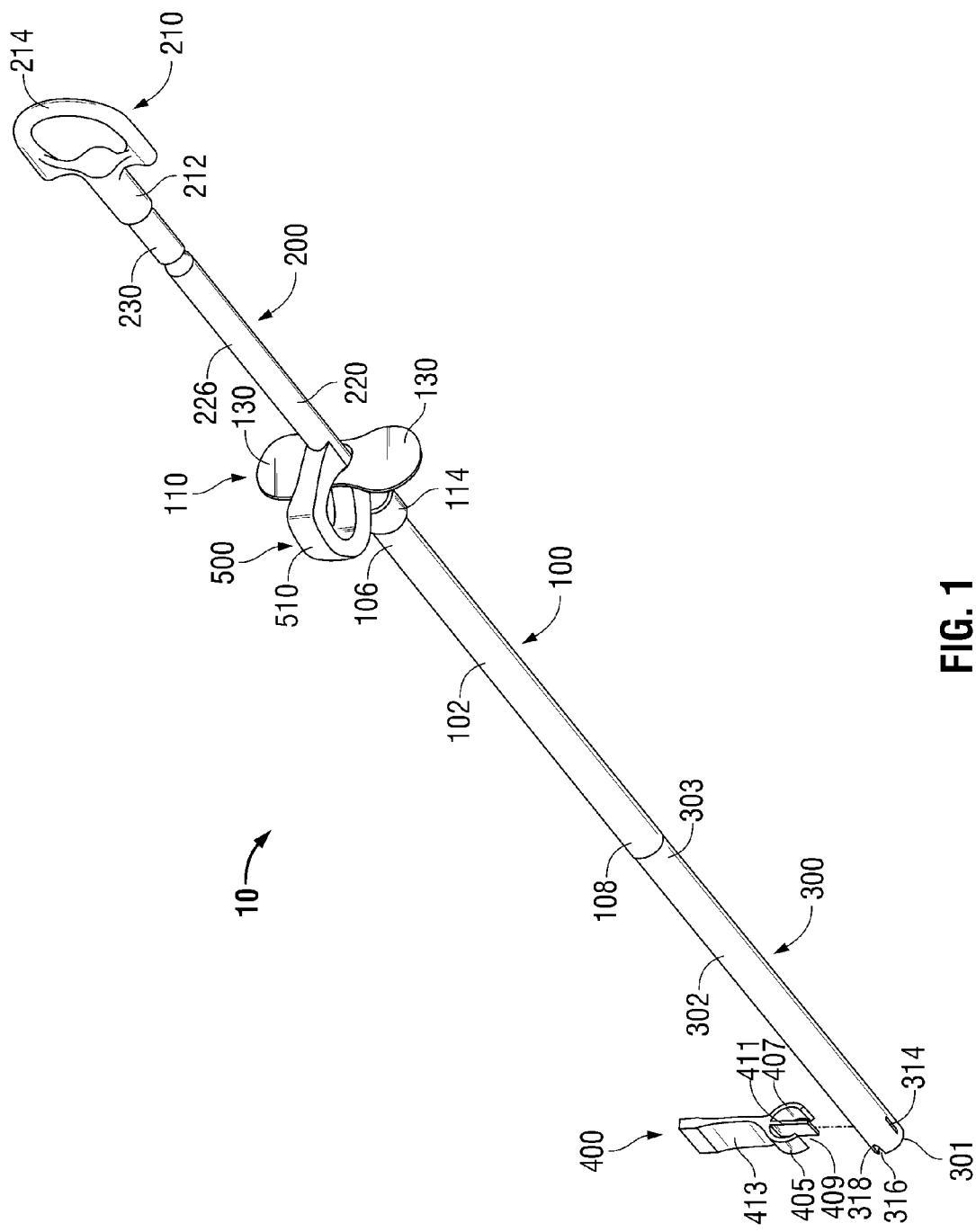
FIG. 1 is a perspective view of one embodiment of a surgical retrieval apparatus in accordance with the present disclosure.

Various embodiments of the presently disclosed surgical retrieval apparatus, and methods of using the same, will now be described in detail with reference to the drawings wherein like references numerals identify similar or identical elements. In the drawings, and in the following description, the term "proximal" should be understood as referring to the end of the apparatus, or component thereof, that is closer to the clinician during proper use, while the term "distal" should be understood as referring to the end that is farther from the clinician, as is traditional and conventional in the art.

Turning now to FIGS. 1-5A, a surgical retrieval apparatus in accordance with the present disclosure is shown generally identified by reference numeral 10. Surgical retrieval apparatus 10 generally includes a tube assembly 100, a plunger assembly 200, a cartridge assembly 300, a lock tab 400, and a pull ring 500. Tube assembly 100 and plunger assembly 200 are configured as reusable components. More specifically, tube assembly 100 and plunger assembly 200 are formed from strong, durable, sterilizable material(s), e.g., stainless steel, such that tube assembly 100 and plunger assembly 200 may be sterilized and reused. Cartridge assembly 300, lock tab 400, and pull ring 500, on the other hand, are configured as single-use, limited use, or disposable components. As will be described below, the disposable components of surgical retrieval apparatus 10, e.g., cartridge assembly 300, lock tab 400, and pull ring 500, are easily and efficiently engagable/disengagable from the reusable components, e.g., tube assembly 100 and plunger assembly 200, to facilitate disassembly of the used, or first set of disposable components from the reusable components after use and assembly of a new, or second set of disposable components with the sterilized reusable components in preparation for subsequent use.

Figure 2:
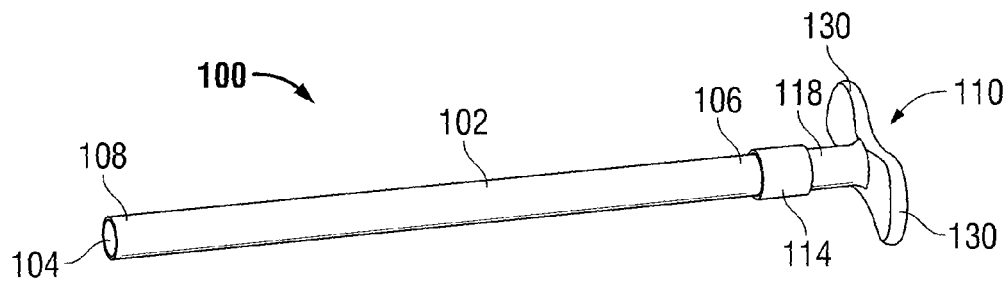
FIG. 2 is a perspective view of a tube assembly of the surgical retrieval apparatus of FIG. 1.

Referring to FIGS. 1 and 2, tube assembly 100 includes an elongated tubular member 102 (although other configurations, e.g., rectangular, polygonal, etc., are contemplated) having a lumen 104 extending therethrough, a grasping portion 110 disposed at proximal end 106 of elongated tubular member 102, and an annular cuff 114 disposed about elongated tubular member 102 towards proximal end 106 thereof but spaced-apart from grasping portion 110 so as to define an exposed proximal segment 118 of elongated tubular member 102 between annular cuff 114 and grasping portion 110. Lumen 104 of elongated tubular member 102 defines a diameter sufficient to permit passage of at least a portion of plunger assembly 200 therethrough. As mentioned above, tube assembly 100 may be formed from stainless steel, or other suitable strong, durable, sterilizable material. Tube assembly 100 may be monolithically formed as a single component, or each of the components, e.g., elongated tubular member 102, grasping portion 110 and annular cuff 114, may be welded together or engaged with one another via any other suitable process.

Elongated tubular member 102 of tube assembly 100 includes an annular recess 120 (FIGS. 7A-7B) defined within the interior surface thereof and disposed towards distal end 108 of elongated tubular member 102. Annular recess 120, as will be described below, is configured to facilitate engagement of cartridge assembly 300 and elongated tubular member 102 of tube assembly 100 at distal end 108 of elongated tubular member 102.

Grasping portion 110 of tube assembly 100 includes a pair of opposed flanges 130 extending radially outwardly from proximal end 106 of elongated tubular member 102. Flanges 130 define oval-shaped configurations and are configured to facilitate grasping of tube assembly 100. More specifically, this configuration of grasping portion 110 of tube assembly 100 permits the clinician to grasp tube assembly 100 in numerous configurations, while still being able to fully manipulate and operate surgical retrieval apparatus 10. However, other configurations of grasping portion 110 are also contemplated, e.g., greater than two flanges 130 may be provided, flanges 130 may define different configurations, flanges 130 may be configured as finger loops, etc.

Figure 3:
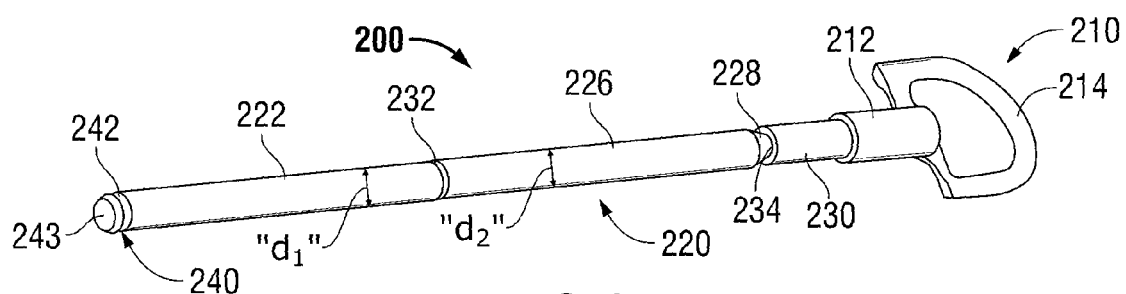
FIG. 3 is a perspective view of a plunger assembly of the surgical retrieval apparatus of FIG. 1.
Figure 8:
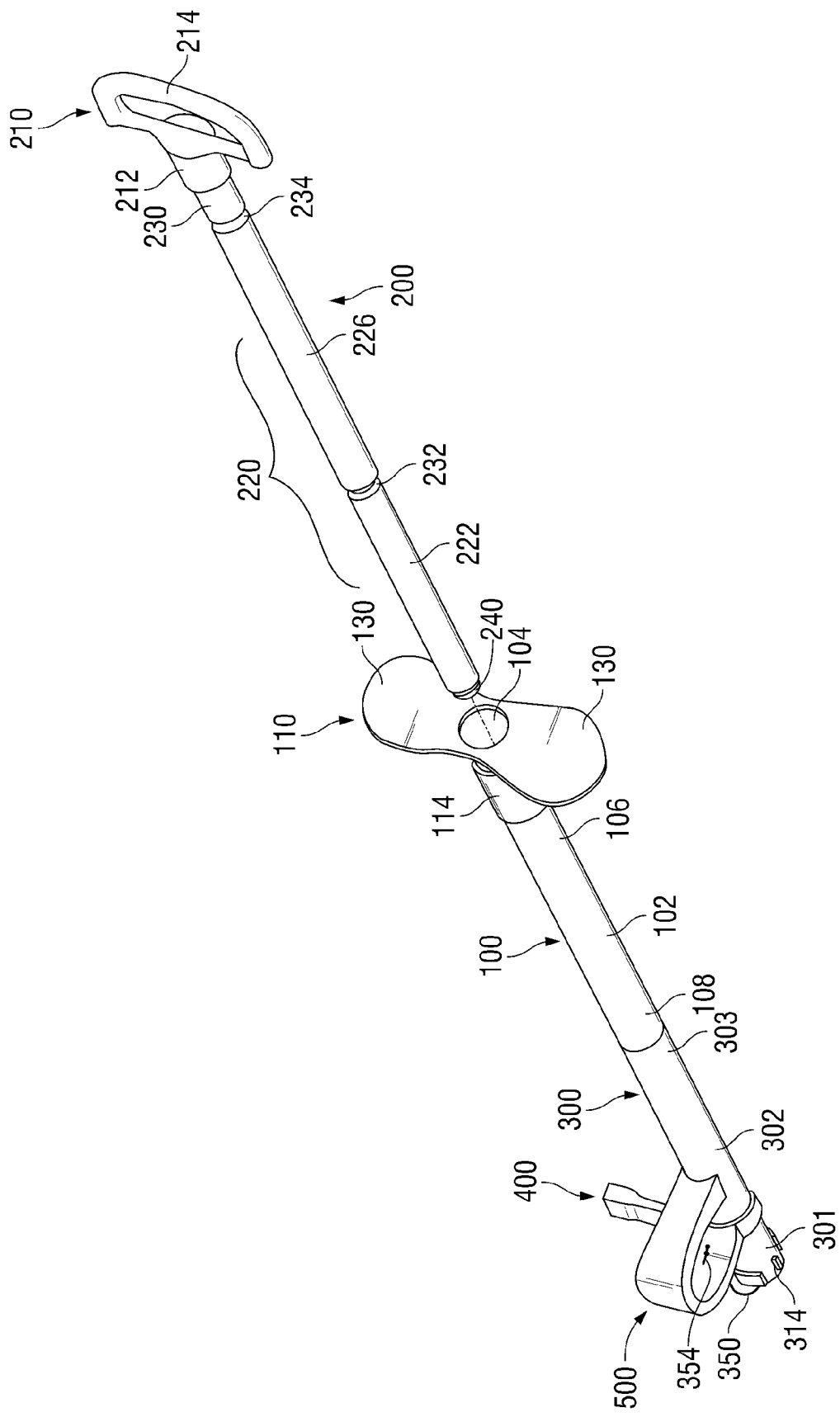
FIG. 8 is a perspective view of the surgical retrieval apparatus with the plunger assembly spaced-apart from the tube assembly.
Figure 19A:
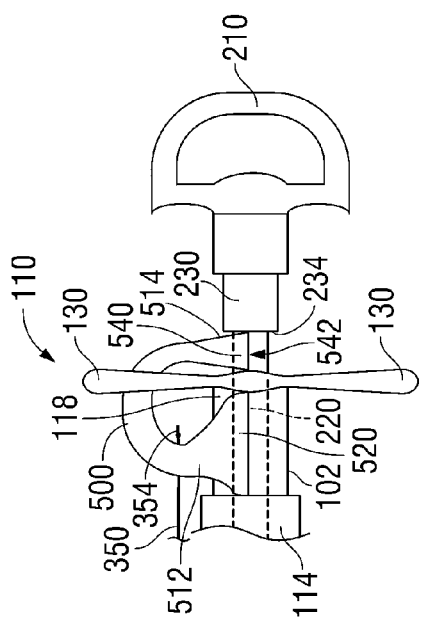
FIG. 19A is a side view of a proximal end of the tube assembly with the plunger assembly inserted therethrough in a distal position.

With reference now to FIGS. 1 and 3, plunger assembly 200 includes a handle 210 and an elongated shaft 220 extending distally from handle 210. Handle 210 and elongated shaft 220 may be formed from stainless steel (or other suitable material(s)) and/or may be monolithically formed, welded, or otherwise engaged with one another. Handle 210 includes a base 212 and a finger ring 214 extending proximally from base 212 that is configured to facilitate grasping and translating plunger assembly 200. Other configurations of handle 210 are also contemplated, e.g., handle 210 may include grasping flanges (not shown) or other suitable grasping features. As will be described below, plunger assembly 200 is insertable into and is translatable relative to tube assembly 100 amongst a disengaged position (FIG. 8), wherein plunger assembly 200 is disengaged from surgical retrieval apparatus 10, a proximal use position (FIG. 11), wherein plunger assembly 200 is inserted partially through tube assembly 100 and into engagement with end effector assembly 320 (FIG. 5A) of cartridge assembly 300, a distal use position (FIGS. 14A and 19A), wherein plunger assembly 200 is inserted further through tube assembly 100 to deploy end effector assembly 320 (FIG. 5A) of cartridge assembly 300, and an eject position (FIG. 19B), wherein plunger assembly 200 is inserted further into tube assembly 100 to eject, disengage, or separate cartridge assembly 300 from tube assembly 100.

Elongated shaft 220 of plunger assembly 200 includes a distal segment 222 defining a diameter "$d_1$," a proximal segment 226 defining a diameter "$d_2$," and a neck 230 interconnecting proximal segment 226 and base 212 of handle 210. Diameters "$d_1$" and "$d_2$" are sufficiently small so as to permit translation of distal and proximal segments 222, 226, respectively, of elongated shaft 220 of plunger assembly 200 through lumen 104 of elongated tubular member 102 of tube assembly 100. Diameter "$d_2$" is greater than diameter "$d_1$" such that elongated shaft 220 defines a first step 232 at the interface between proximal segment 226 (which defines relatively larger diameter "$d_2$") and distal segment 222 (which defines relatively smaller diameter "$d_1$"). As can be appreciated, the step height of first step 232 is equal to the difference in diameter between proximal segment 226 and distal segment 222. Further, as will be detailed below, first step 232 defines a recess 233a and an angled surface 233b configured to facilitate ejection of cartridge assembly 300 from tube assembly 100 (see FIGS. 20A-20B).

Proximal segment 226 of elongated shaft 220 further includes a tapered proximal end 228 such that a second step 234 is formed at the interface between proximal segment 226 and neck 230. Neck 230 may define a diameter similar to that of proximal segment 226 such that second step 234 defines a step height equal to the difference between the diameter "$d_2$" of proximal segment 226 and the minimum diameter of tapered proximal end 228 of proximal segment 226. Alternatively, neck 230 may define a diameter greater than that of proximal segment 226 such that second step 234 defines an increased step height.

Figure 9A:
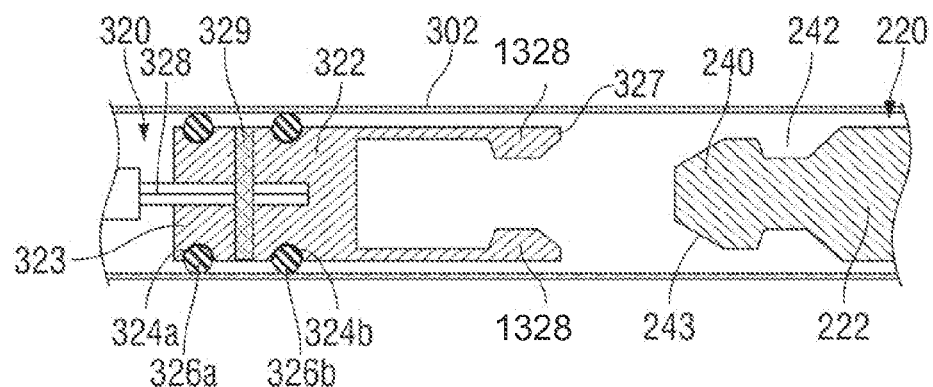
FIG. 9A is a longitudinal, cross-sectional view of a proximal end of the cartridge assembly with the cartridge assembly and the plunger assembly disengaged from one another.
Figure 9B:
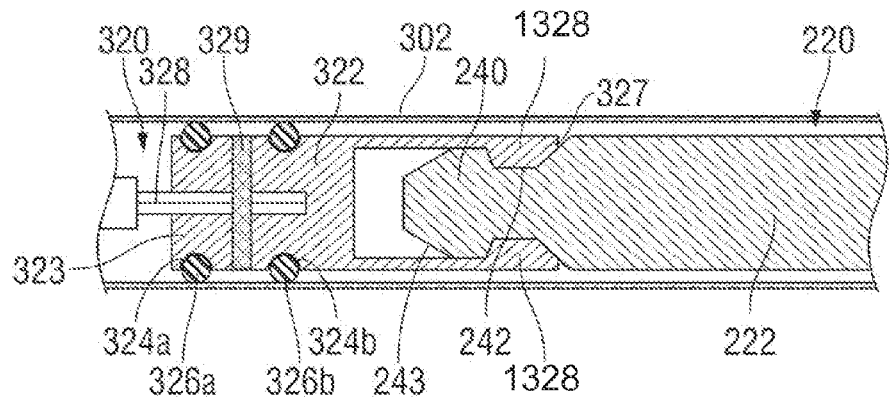
FIG. 9B is a longitudinal, cross-sectional view of the proximal end of the cartridge assembly with the cartridge assembly and the plunger assembly engaged with one another.

Referring additionally to FIGS. 9A and 9B, distal segment 222 of elongated shaft 220 includes a distal head portion 240 extending distally from distal segment 222. An annular recess 242 is defined within the exterior surface of distal segment 222 between distal segment 222 and distal head portion 240. Distal head portion 240 further defines an angled distal edge 243. Distal head portion 240 may be monolithically formed within distal segment 222 of elongated shaft 220, may be welded thereto, or may be engaged to distal segment 222 in any other suitable fashion. Distal head portion 240, angled distal edge 243, and annular recess 242, as will be described below, are configured to facilitate engagement of elongated shaft 220 of plunger assembly 200 and end effector assembly 320 (FIG. 5) of cartridge assembly 300 with one another.

Figure 4:
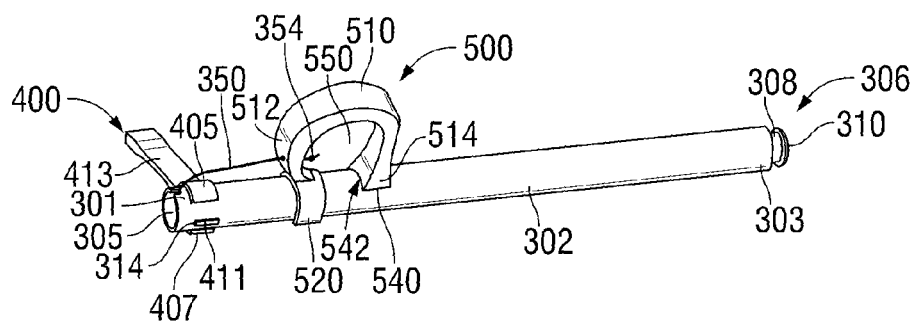
FIG. 4 is a perspective view of a cartridge assembly of the surgical retrieval apparatus of FIG. 1.
Figure 5A:
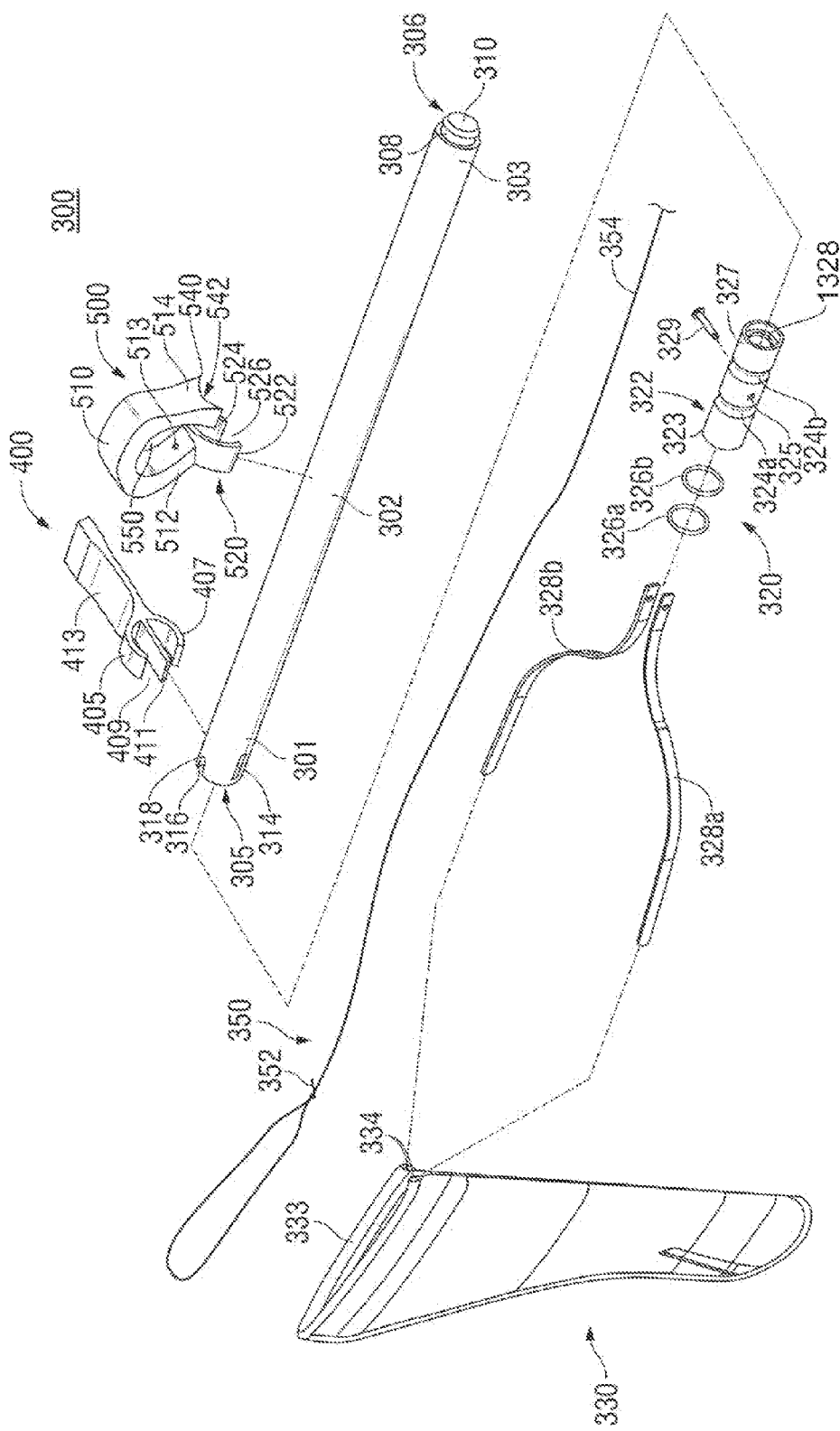
FIG. 5A is a perspective view of the cartridge assembly of FIG. 4, shown with parts separated.

Referring to FIGS. 1, 4 and 5A, cartridge assembly 300 includes a tubular housing 302 (although other configurations, e.g., rectangular, polygonal, etc., are contemplated) and an end effector assembly 320 slidably disposed within tubular housing 302. Tubular housing 302 includes a distal end 301, a proximal end 303, and a lumen 305 extending therethrough. Proximal end 303 of tubular housing 302 includes a cap 306 extending proximally therefrom that is configured to engage annular recess 120 (FIGS. 7A-7B) defined within elongated tubular member 102 to engage cartridge assembly 300 and tube assembly 100 with one another. Cap 306, as will be described below, includes a neck 308 and a head 310 that defines a tapered configuration having one or more relief slots 312 defined therein (see FIGS. 7A-7B). Distal end 301 of tubular housing 302 includes a lock slot 314 defined therethrough that is configured to receive lock tab 400. Distal end 301 of tubular housing 302 further includes a cord slot 316 including a cord aperture 318 that is configured to receive cinch cord 350 therethrough.

Cartridge assembly 300 is configured for insertion through an opening in tissue, e.g., through a surgical access portal 600 (FIGS. 13A-13B) or cannula 600' (FIGS. 13C-13D) disposed within an opening or incision "I" (FIGS. 13A-13B) in tissue "T" (FIGS. 13A-13B), and into an internal surgical site, or body cavity "C." As such, it is envisioned that tubular housing 302 of cartridge assembly 300 and elongated tubular member 102 of tube assembly 100 together define a sufficient length such that cartridge assembly 300 and tube assembly 100 may be advanced at least partially through the incision "I" (FIGS. 13A-13B) and into the internal body cavity "C" to a position adjacent a tissue specimen "S" (FIG. 14B) to be removed, while grasping portion 110 of tube assembly 100 and handle 210 of plunger assembly 200 remain external of the patient.

End effector assembly 320 is slidably disposed within tubular housing 302 of cartridge assembly 300 and generally includes a push bar 322, a pair of arms 328a, 328b (collectively arms 328), and a specimen retrieval bag 330. End effector assembly 320 is longitudinally translatable through and relative to tubular housing 302 of cartridge assembly 300 between an insertion/removal or retracted position (FIG. 12), wherein arms 328 and specimen retrieval bag 330 are disposed within tubular housing 302, and an extended or deployed position (FIG. 14B), wherein arms 328a, 328b extend distally from tubular housing 302 to deploy specimen retrieval bag 330. As will be described below, movement of plunger assembly 200 between the proximal use position (FIG. 13A) and the distal use position (FIG. 14A) transitions end effector assembly 320 between the retracted position (FIGS. 12 and 13B) and the deployed position (FIG. 14B).

Arms 328a, 328b of end effector assembly 320 are coupled to distal end 323 of push bar 322 via pin 329 and are movable, upon translation of push bar 322, between the retracted position, wherein arms 328a, 328b are retained in a substantially-straight configuration in close proximity to one another within tubular housing 302 of cartridge assembly 300, and the deployed position, wherein arms 328a, 328b extend distally from tubular housing 302 to define a spaced-apart, curvate configuration, (see FIGS. 5A and 14B), although other configurations, e.g., linear arms, are also contemplated. Arms 328a, 328b of end effector assembly 320 are further configured for releasably retaining specimen retrieval bag 330 thereon. More specifically, arms 328a, 328b are configured for removable positioning within loop 334 formed at open end 333 of specimen retrieval bag 330 to retain specimen retrieval bag 330 thereon. Arms 328a, 328b may be biased toward the spaced-apart, curvate configuration such that, upon reaching the deployed position, e.g., upon extension of arms 328a, 328b from tubular housing 302, arms 328a, 328b are automatically deployed, i.e., arms 328a, 328b are resiliently returned, to the spaced-apart curvate configuration to transition and maintain specimen retrieval bag 330 in an open condition.

Push bar 322, as mentioned above, is slidably disposed within tubular housing 302 of cartridge assembly 300 and includes a pair of opposed apertures 325 defined therethrough that are configured to receive pin 329 therethrough for engaging arms 328a, 328b to push bar 322 at distal end 323 of push bar 322. Push bar 322 further includes a pair of ring-shaped recesses 324a, 324b defined therein that are configured to receive first and second O-rings 326a, 326b, respectively. O-rings 326a, 326b are configured for frictionally retaining push bar 322 in position within tubular housing 302 to inhibit accidental or inadvertent deployment or retraction of end effector assembly 320. However, the frictional force between O-rings 326a, 326b and tubular housing 302 is sufficiently small so as to permit translation of end effector assembly 320 through tubular housing 302, e.g., upon translation of plunger 200 (FIG. 3) between the proximal use position and the distal use position. Further, the interface between O-rings 326a, 326b and an inner wall of tubular housing 302 provides a substantially fluid-tight barrier.

Push bar 322 further includes a hollow proximal end 327 that defines an annular protrusion 1328 on an internal surface thereof. Annular protrusion 1328, as will be detailed below, is configured for engagement within annular recess 242 defined between distal head portion 240 and distal segment 222 of plunger assembly 220 (see FIGS. 3, 9A, and 9B) to engage plunger assembly 200 (FIG. 3) and end effector assembly 320 with one another. Push bar 322 may be formed from a resilient material, e.g., a biocompatible polymer or other suitable material, to facilitate engagement of plunger assembly 200 (FIG. 3) and end effector assembly 320 with one another.

Figure 5B:
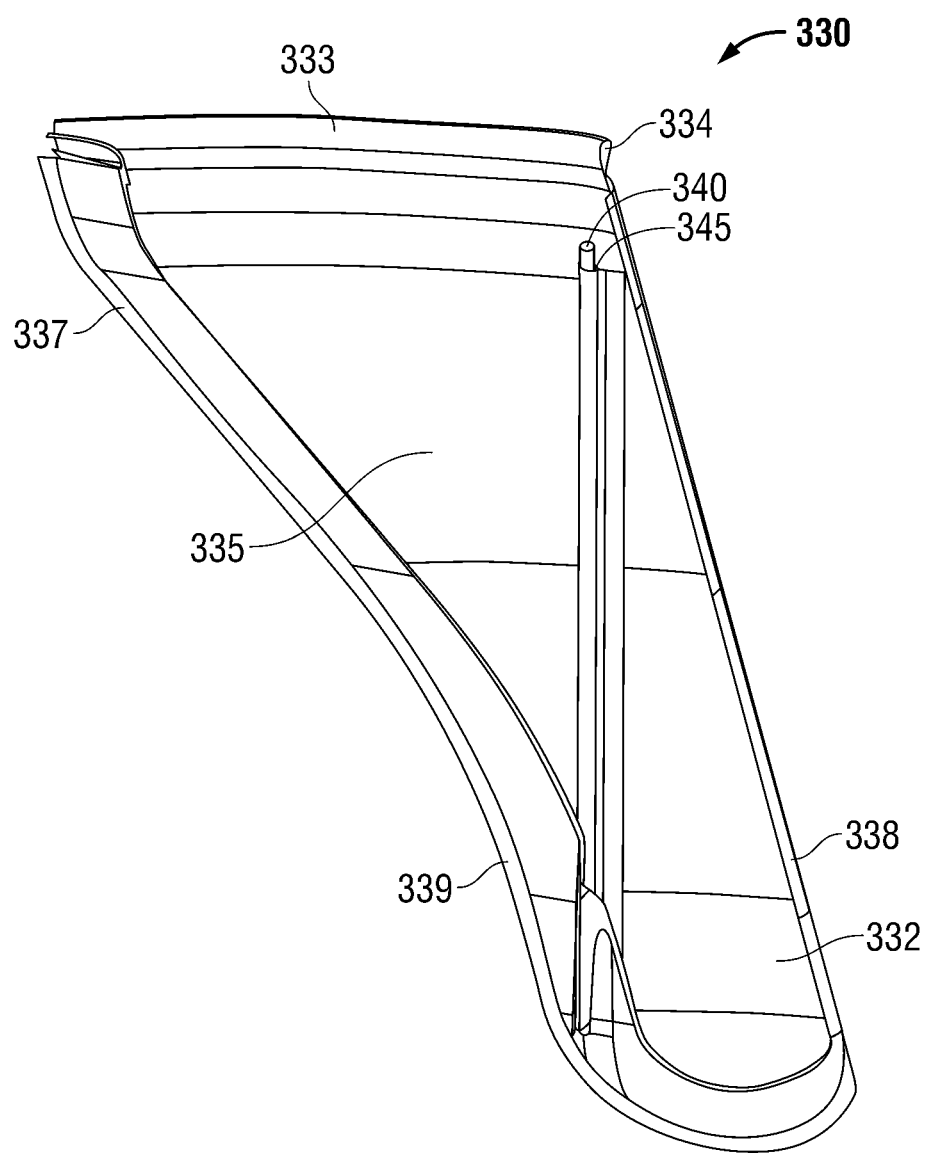
FIG. 5B is a side, cut-away view of one embodiment of a specimen retrieval bag configured for use with the cartridge assembly of FIG. 4.

With reference to FIGS. 5A and 5B, specimen retrieval bag 330 is removably engagable with arms 328 of end effector assembly 320, and depends therefrom. More specifically, specimen retrieval bag 330 is folded over at an open end 333 thereof to form a loop 334 around the outer periphery thereof. Specimen retrieval bag 330 is transitionable between a rolled-up, or storage position corresponding to the retracted position of end effector assembly 320, and an open, or deployed position corresponding to the deployed position of end effector assembly 320. A cinch cord 350 is disposed through loop 334 of specimen retrieval bag 330. First and second ends 352, 354, respectively, of cinch cord 350 extend proximally from loop 334 of specimen retrieval bag 330. One of the ends, e.g., first end 352, is looped, or otherwise disposed about second end 354 thereof (see FIG. 5A), while the other end, e.g., second end 354, extends proximally though cord aperture 318 of cord slot 316 defined within distal end 301 of tubular housing 302 of cartridge assembly 300, ultimately engaging, i.e., knotting about, pull ring 500. Accordingly, as will be described in greater detail below, upon proximal translation of pull ring 500 relative to end effector assembly 320, cinch cord 350 is likewise pulled proximally to tension cinch cord 350 such that specimen retrieval bag 330 is cinched closed.

With continued reference to FIGS. 5A and 5B, it is envisioned that specimen retrieval bag 330 be formed from any suitable bio-compatible material (or materials), e.g., 30 Denier Ripstop Nylon, configured to retain a specimen of tissue "S" (FIG. 18) therein and to inhibit the passage of fluids and biological materials therethrough. The bag 330 can include a coating, such as a polyurethane coating, to prevent egress of fluid if a permeable bag is utilized or to improve the impermeability. The coating can be placed on the inner surface and/or the outer surface of the bag 330. Specimen retrieval bag 330 includes a lower portion 332 having a minimized cross-section configured to re-orient or re-position the specimen of tissue "S" (FIG. 18) within specimen retrieval bag 330 to facilitate removal of specimen retrieval bag 330 from an internal body cavity, and a relatively expansive upper portion 335 configured to facilitate positioning of relatively large specimen of tissue "S" (FIG. 18) within specimen retrieval bag 330. In other words, lower portion 332 has a smaller transverse dimension than upper portion 335. More specifically, upper portion 335 of specimen retrieval bag 330 has a first side 336 and a generally angled side 337 disposed opposite first side 336. Angled side 337 tapers inwardly such that the transverse dimension of upper portion 335 of specimen retrieval bag 330 progressively decreases toward the lower portion 332 of specimen retrieval bag 330. Wall 338, which opposes wall 339 in lower portion 332 of specimen retrieval bag 330, extends substantially parallel to wall 339 such that the transverse dimension of lower portion 332 remains substantially constant along a length thereof. Alternatively, specimen retrieval bag 330 may be formed in various other configurations depending on the intended use of specimen retrieval bag 330.

Specimen retrieval bag 330 may in some embodiments further include a high-friction mesh material disposed on an inner surface thereof to facilitate retention of the tissue specimen "S" (FIG. 18) therein. In other embodiments, the bag shape is relied on to retain the specimen "S" (FIG. 18) and a smooth inner surface is provided to enable easy passage of the tissue specimen "S" (FIG. 18) from the upper loading area, i.e., upper portion 335, of the bag 330 to the lower shaping region, i.e., lower portion 332, of the bag 330 during extraction.

Specimen retrieval bag 330 further includes, in some embodiments, a channel 345 formed therein. The channel 345 can be formed as integral with the bag material or alternatively can be in the form of a separate tube attached to the bag 330, e.g. attached to an inner surface. The channel 345 includes at least one opening or slot (not explicitly shown) along its length to allow the passage of air into the channel 345. Preferably, a plurality of slots or openings (not explicitly shown) is provided to enable communication between the air and/or fluid in the bag 330 and the interior of the channel 345. The channel 345 in some embodiments can also terminate at its distal end spaced from the bottom of the bag 330 to communicate at a distal opening with the interior of the bag 330 to provide another path for the escape of air fluid. Further, the proximal end of channel 345, in some embodiments, may be open to communicate with the exterior of the bag 330.

A support member (or support members) 340 may be disposed within specimen retrieval bag 330 to help inhibit collapse of the channel 345 and/or for biasing specimen retrieval bag 330 toward an open position upon deployment from surgical retrieval apparatus 10. Support member 340 may be formed from, for example, an open cell foam, or other suitable material that enables the passage of air and/or fluid therethrough, thus allowing air and/or fluid to escape specimen retrieval bag 330 upon collapse or compression of specimen retrieval bag 330 to reduce the internal pressure within specimen retrieval bag 330. More specifically, the open cell foam is preferably of a transverse cross-section less than the transverse cross-section of the channel 345. In this manner, air and/or fluid entering the channel 345 from the bag 330 can flow around the foam material through the channel 345. Note that due to the open cell foam, the air or fluid can also flow through the open cell foam itself. This way, if the channel 345 collapses or is compressed during specimen retrieval, air and fluid can still escape. The escape of air and fluid is caused as the pressure is applied to the bag 330 during withdrawal through access portal 600 (FIGS. 13A-13B), or other opening in tissue "T" (FIGS. 13A-13B). As the bag 330 is compressed, the air and/or fluid is forced proximally through the channel 345, exiting the open proximal end thereof. Thus, this decrease in pressure prevents balling of the specimen "S" (FIG. 18) at the bottom of the bag 330 and facilitates removal. Other suitable specimen retrieval bags (not shown) may also be provided for use in conjunction with surgical retrieval apparatus 10.

Figure 5C:
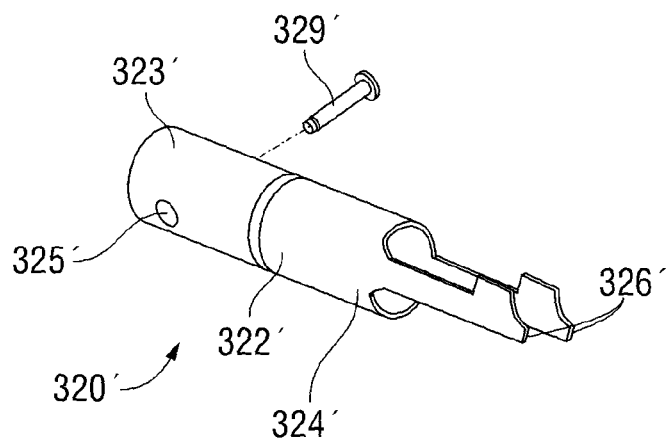
FIG. 5C is perspective view of another embodiment of a end effector assembly configured for use with the cartridge assembly of FIG. 4.

With reference to FIG. 5C in conjunction with FIGS. 1-5A, another embodiment of an end effector assembly 320' configured for use with cartridge assembly 300 (FIG. 5A) is shown. End effector assembly 320', similar to end effector assembly 320 (FIG. 5A), is configured for slidable positioning within tubular housing 302 of cartridge assembly 300 such that end effector assembly 320' may be longitudinally translated through and relative to tubular housing 302 of cartridge assembly 300 between an insertion/removal or retracted position (FIG. 12), and an extended or deployed position (FIG. 14B).

End effector assembly 320' is configured to engage a pair of arms (similar to arms 328a, 328b of end effector assembly 320) that, in turn, are configured to releasably retain a specimen retrieval bag, e.g., specimen retrieval bag 330, specimen retrieval bag 330' (FIG. 5D), or any other suitable specimen retrieval bag, thereon. More specifically, arms 328a, 328b are configured for engagement within distal end 323' of push bar 322' of end effector assembly 320' via pin 329' such that arms 328a, 328b are movable upon translation of push bar 322' between the refracted position and the deployed position, similarly as described above with respect to end effector assembly 320. Arms 328a, 328b, as mentioned above, are configured to releasably retain specimen retrieval bag 330 (or specimen retrieval bag 330' (FIG. 5D) or any other suitable specimen retrieval bag) thereon.

Push bar 322' further includes one or more proximally-extending engagement fingers 326', e.g., two engagement fingers 326', extending from proximal end 324' thereof that are configured for engagement within annular recess 242 of distal head portion 240 of plunger assembly 200 to engage plunger assembly 200 and end effector assembly 320 with one another. Engagement fingers 326' may be formed from a resilient material, e.g., a biocompatible polymer or other suitable material, to facilitate engagement of plunger assembly 200 and end effector assembly 320' with one another.

The use and operation of end effector assembly 320' in conjunction with cartridge assembly 300 (FIG. 5A) is substantially similar to that of end effector assembly 320, as will be described below. Therefore, the use and operation of end effector assembly 320' will not be described herein to avoid unnecessary repetition.

Figure 5D:
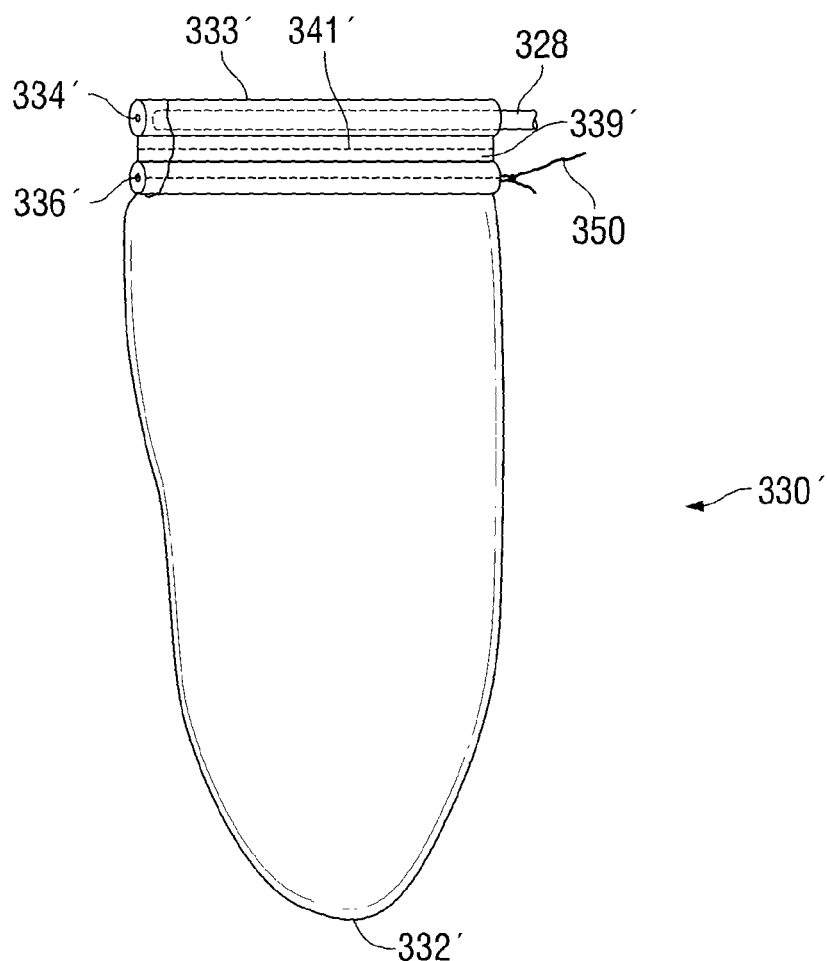
FIG. 5D is a side view of another embodiment of a specimen retrieval bag configured for use with the cartridge assembly of FIG. 4.

Turning now to FIG. 5D, in conjunction with FIG. 5A, another embodiment of a specimen retrieval bag 330' configured for use with end effector assembly 320 (or end effector assembly 320' (FIG. 5C)) is shown. Specimen retrieval bag 330' includes a closed end portion 332' and an openable and closable end portion or mouth 333'. Mouth 333' of specimen retrieval bag 330' is defined by an upper sleeve 334' and a lower sleeve 336' interconnected by an intermediate portion 339'. Intermediate portion 339' is weakened by perforation or scoring 341' to facilitate tearing of the intermediate portion 339' along scored line(s) 341'.

With continued reference to FIG. 5D, in conjunction with FIG. 5A, upper sleeve 334' of specimen retrieval bag 330' is adapted to receive arms 328 therein, while lower sleeve 336' is adapted to receive cinch cord 350 therethrough. Scoring 341' is adapted to tear upon proximal pulling of cinch cord 350 to close mouth 333' such that detachment of specimen retrieval bag 330' from arms 328 is effected simultaneously, or nearly simultaneously, with the closure of mouth 333'. Further detail of specimen retrieval bag 330' can be found in U.S. Pat. No. 5,647,372 to Tovey et al., the entire contents of which is hereby incorporated by reference herein.

Referring again to FIGS. 1 and 5A, lock tab 400 includes a pair of outer, curvate fingers 405, 407 defining a generally annular passageway 409 therebetween, and a central finger 411 extending between outer fingers 405, 407 to bisect annular passageway 409. Lock tab 400 is configured for positioning about distal end 301 of tubular housing 302 of cartridge assembly 300 to inhibit end effector assembly 320 from being transitioned to the deployed position. More specifically, lock tab 400 is configured for positioning such that central finger 411 extends through lock slot 314 of tubular housing 302 and into lumen 305 thereof to inhibit deployment of end effector assembly 320, while outer fingers 405, 407 of lock tab 400 are disposed about distal end 301 of tubular housing 302 to retain lock tab 400 in position about cartridge assembly 300. Outer fingers 305, 307 may be configured such that the dimensions of passageway 309 generally approximate or are slightly smaller than the dimensions of tubular housing 302 of cartridge assembly 300 such that outer fingers 305, 307 are resiliently flexed outwardly to receive tubular housing 302 therebetween. Accordingly, the bias of outer fingers 305, 307 inwardly towards their at-rest position facilitates the retention of lock tab 400 about distal end 301 of tubular housing 302 of cartridge assembly 300.

Continuing with reference to FIGS. 1 and 5A, pull ring 500 includes a finger loop 510 defining an aperture 550 therethrough. Finger loop 510 includes a distal cuff 520 at distal end 512 thereof and a proximal contact member 540 at proximal end 514 thereof. Second end 354 of cinch cord 350 extends through an aperture defined through finger loop 510 of pull ring 500 and is knotted on the other side thereof. Alternatively, second end 354 of cinch cord 350 may be otherwise secured to finger loop 510 of pull ring 500 in any suitable fashion, e.g., cinch cord 350 may be tied about finger loop 510. Pull ring 500 is configured initially to be positioned about cartridge assembly 300 towards distal end 301 thereof (see FIG. 8) and is movable from this initial position to a use position (see FIG. 11), wherein pull ring 500 is disposed adjacent proximal end 106 of tube assembly 100. Ultimately, pull ring 500 is disengagable from tube assembly 100, as will be described in greater detail below, and is proximally translatable relative to surgical retrieval apparatus 10 to cinch closed specimen retrieval bag 330.

Figure 11:
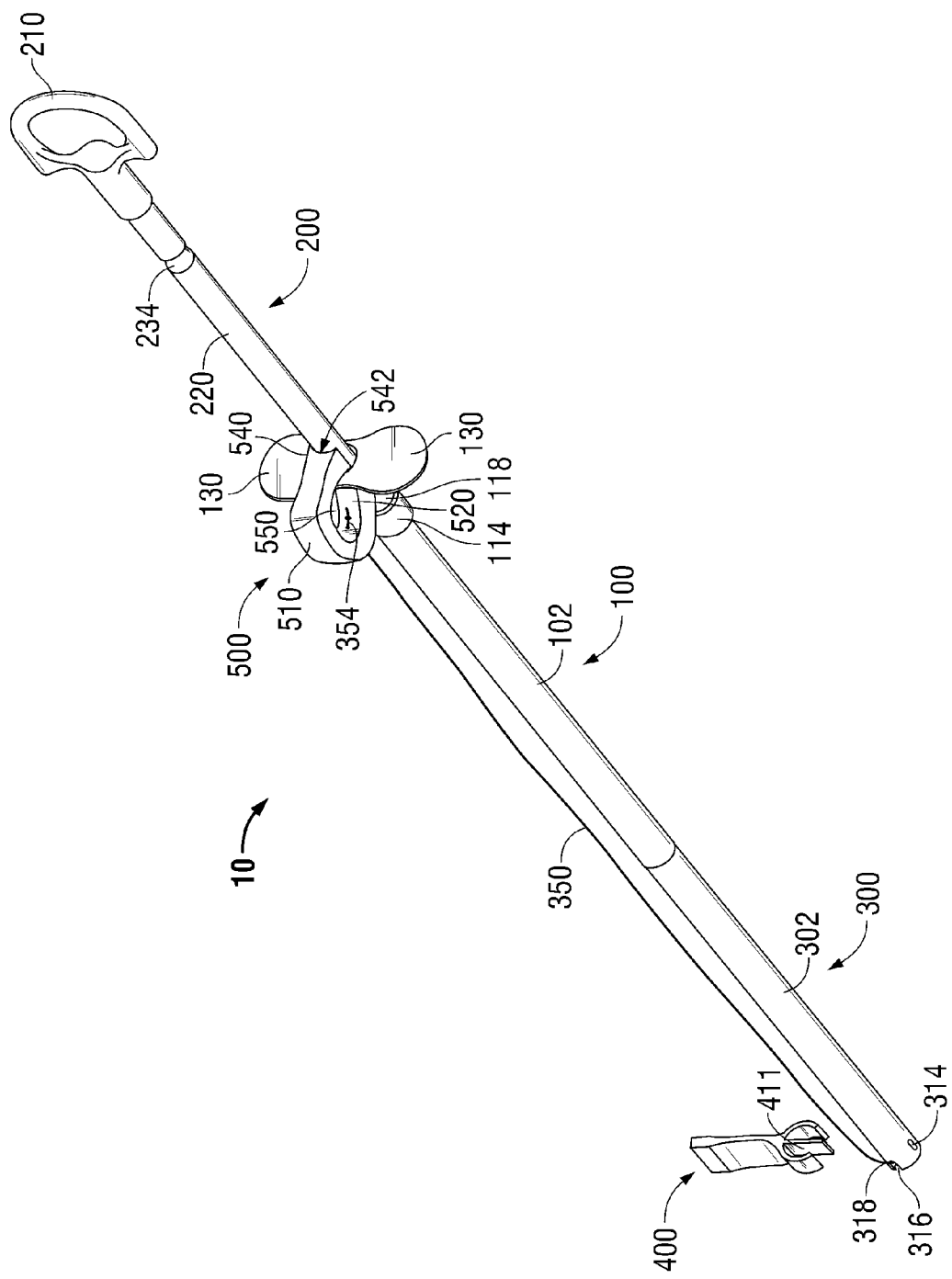
FIG. 11 is a perspective view of the surgical retrieval apparatus with the plunger inserted into the tube assembly and engaged with the cartridge assembly.

Aperture 550 of pull ring 500 is dimensioned to receive a finger of the user to facilitate grasping and translating pull ring 500. Distal cuff 520 of pull ring 500 includes a pair of spaced-apart fingers 522, 524, that, similar to fingers 405, 407 of lock tab 400, are dimensioned to define a passageway 526 that generally approximates or is slightly smaller than the dimensions of tubular housing 302 of cartridge assembly 300 and elongated tubular member 102 of tube assembly 100 such that spaced-apart fingers 522, 524 may be engaged about either tubular housing 302 or elongated tubular member 102 to retain pull ring 500 thereon. Proximal contact member 540 includes an arcuate surface 542 that is configured to sit about a portion of tubular housing 302 or elongated tubular member 102, depending on the position of pull ring 500, e.g., the initial position (FIG. 8) or the use position (FIG. 11).

Turning now to FIGS. 6-21, the use and operation of surgical retrieval apparatus 10 will be described along with a more detailed description of the working components of surgical retrieval apparatus 10. As mentioned above, cartridge assembly 300 (including tubular housing 302 and end effector assembly 320), lock tab 400, and pull ring 500 are configured as disposable components, while tube assembly 100 and plunger assembly 200 are configured as reusable components. Thus, in preparation for use, a first cartridge assembly 300, lock tab 400 and pull ring 500 are obtained, while tube assembly 100 and plunger assembly 200 are sterilized for reuse. The disposable components, e.g., lock tab 400, pull ring 500, and cartridge assembly 300, may be pre-assembled and packaged together as a disposable component kit, separate from the reusable components (tube assembly 100 and plunger assembly 200). Such a configuration is advantageous in that the user would simply need to obtain a second kit, or set of disposable components for the next use.

Referring to FIGS. 6, 7A and 7B, as mentioned above, the disposable components of surgical retrieval apparatus 10 may be pre-assembled and packaged together in a kit for efficient assembly of the disposable and reusable components of surgical retrieval apparatus 10 for use. More specifically, end effector assembly 320 (FIG. 5A) is initially disposed within tubular housing 302 of cartridge assembly 300 in the retracted position, lock tab 400 is engaged with distal end 301 of tubular housing 302 with central finger 411 extending through lock slot 314, pull ring 500 is positioned about cartridge assembly 300 towards distal end 301 of tubular housing 302, and cinch cord 350 extends from lumen 305 of tubular housing 302 (wherein cinch cord 350 is disposed through loop 334 of specimen retrieval bag 330 of end effector assembly 320), through cord aperture 318 of cord slot 316, ultimately engaging pull ring 500. With this first set of disposable components assembled together and ready for use, tube assembly 100 may be engaged with cartridge assembly 300.

Continuing with reference to FIGS. 6, 7A and 7B, and initially to FIGS. 6 and 7A, in order to engage tube assembly 100 and cartridge assembly 300 with one another, cartridge assembly 300 is approximated relative to tube assembly 100 such that cap 306 of tubular housing 302 of cartridge assembly 300 is inserted proximally into lumen 104 of elongated tubular member 102 of tube assembly 100. Head 310 of cap 306, as mentioned above, tapers in diameter distally to proximally to facilitate insertion of cap 306 into lumen 104 of elongated tubular member 102. Head 310 of cap 306 further includes one or more relief slots 312 defined therein that are configured to permit compression of head 306 to permit passage of head 310 of cap 306 into lumen 104 of elongated tubular member 102. Further, a lip 309 is formed between head 310 and neck 308 of cap 306, the importance of which will be described below.

As cap 306 is inserted into lumen 104 of elongated tubular member 102, proximal end 311a of head 310 is compressed to permit insertion of cap 306 into elongated tubular member 102. Head 310 of cap 306, due to its tapered configuration, defines a minimum diameter at proximal end 311a thereof to facilitate the advancement and compression of cap 306 into lumen 104. Upon further advancement of head of cap 206 into lumen 104, distal end 311b of head 310, which defines the maximum diameter of head 310, is compressed to permit complete passage of head 310 of cap 306 into lumen 104. Relief slot(s) 312 and the angled outer peripheral surface 311c of head 310, as mentioned above, cooperate to facilitate the insertion and compression of head 310 as cap 306 is urged further into lumen 104 of elongated tubular member 102.

As distal end 311b of head 310 enters lumen 104, distal end 311b of head 310 eventually approximates annular recess 120, wherein an audible and/or tactile "snap" or "click" is produced as head 310 is resiliently biased or decompressed back to its initial position and into engagement within annular recess 120. This "snap" or "click" alerts the user that cartridge assembly 300 and tube assembly 100 are securely engaged with one another, inhibiting longitudinal and rotational movement of cartridge assembly 300 and tube assembly 100 relative to one another. In other words, cartridge assembly 300 and tube assembly 100 are engaged with one another by snap-fitting, which provides an audible and/or tactile feedback signal to the user indicating that cartridge assembly 300 and tube assembly 100 are engaged with one another. In this engaged position, as shown in FIG. 7B, distal end 108 of elongated tubular member 102 of tube assembly 100 and proximal end 303 of tubular housing 302 of cartridge assembly 300 abut one another, while the engagement of distal end 311a and lip 309 of head 310 of cartridge assembly 300 within annular recess 120 of tube assembly 100 inhibits disengagement, or withdrawal of cartridge assembly 300 from tube assembly 100, thereby maintaining cartridge assembly 300 and tube assembly 100 in engagement with one another.

Turning now to FIGS. 8-11, with cartridge assembly 300 and tube assembly 100 engaged with one another, as described above, plunger assembly 200 may be inserted through tube assembly 100 and into cartridge assembly 300 to engage plunger assembly 200 and end effector assembly 320 with one another, e.g., plunger assembly 200 may be transitioned from the disengaged position (FIG. 8), wherein plunger assembly 200 is disengaged from surgical retrieval apparatus 10, to the proximal use position (FIG. 11), wherein plunger assembly 200 is operably engaged with end effector assembly 320. During transitioning of plunger assembly 200 to the proximal use position, both lock tab 400 and pull ring 500 remain disposed about distal end 301 of tubular housing 302 of cartridge assembly 300.

In order to engage plunger assembly 200 and end effector assembly 320 with one another, i.e., in order to transition plunger assembly 200 to the proximal use position, shaft 220 of plunger assembly 200 is inserted distally through lumen 104 of elongated tubular member 102 and into lumen 305 of tubular housing 302 of cartridge assembly 300. As shown in FIG. 9A, as shaft 220 is inserted into lumen 305 of tubular housing 302 of cartridge assembly 300, distal head portion 240 of shaft 220 eventually enters hollow proximal end 327 of push bar 322. Upon further distal insertion of plunger assembly 200 towards the proximal use position, as shown in FIG. 9B, distal head portion 240 is compressed and/or hollow proximal end 327 of push bar 322 is expanded such that distal head portion 240 is permitted to pass through annular protrusion 1328 defined within hollow proximal end 327 of push bar 322. Angled edges 243 of distal head portion 240, as mentioned above, facilitate the insertion of distal head portion 240 into hollow proximal end 327 of push bar 322 and through annular protrusion 1328 thereof. Ultimately, distal head portion 240 of shaft 220 passes through annular protrusion 1328 of push bar 322 such that annular recess 242, which is defined between distal head portion 240 and distal segment 222 of shaft 220, and annular protrusion 1328 of push bar 322 are resiliently biased into engagement with one another. More specifically, as distal head portion 240 of shaft 220 is decompressed and/or as hollow proximal end 327 of push bar 322 is returned from its expanded state, annular protrusion 1328 and annular recess 242 are engaged with one another to engage end effector assembly 320 and plunger assembly 200 with one another. Further, an audible and/or tactile "snap" or "click" may be produced upon snap-fit engagement of shaft 220 and push bar 322 with one another, e.g., upon engagement annular protrusion 1328 within annular recess 242. This "snap" or "click" provides an audible and/or tactile feedback signal to the user indicating that plunger assembly 200 and end effector assembly 320 are engaged with one another.

In the engaged position, as shown in FIG. 9B, push bar 322 is retained in engagement with shaft 220 due to the engagement of annular protrusion 1328 of hollow proximal end 327 of push bar 322 within annular recess 242 defined between distal head portion 240 and distal segment 222 of shaft 220, thus maintaining a secure engagement between plunger assembly 200 and end effector assembly 320. Annular protrusion 1328 and annular recess 242 may further include complementary features, e.g., similarly angled surfaces, or other features, such that the interior surface of hollow proximal end 327 of push bar 322 forming annular protrusion 1328 and the outer surface of shaft 220 forming annular recess 242 substantially mate with one another.

Figure 10:
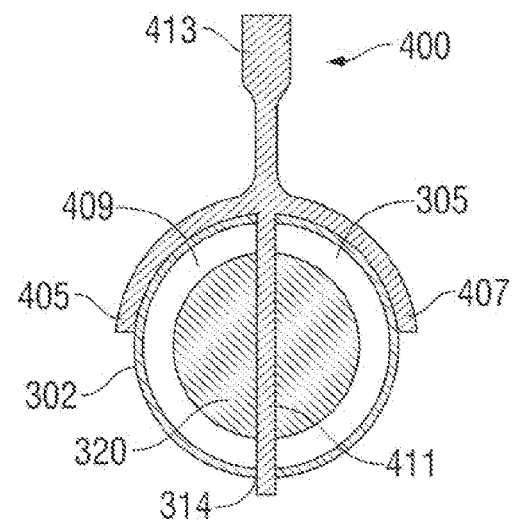
FIG. 10 is a transverse, cross-sectional view of the cartridge assembly including a lock tab engaged thereon.

Referring also to FIG. 10, as mentioned above, lock tab 400 remains engaged about distal end 301 of tubular housing 302 during engagement of plunger assembly 200 and end effector assembly 320 with one another. That is, with central finger 411 of lock tab 400 extending through lock slot 314 of tubular housing 302 and into lumen 305 thereof, deployment of end effector assembly 320 is inhibited. Accordingly, push bar 322 is inhibited from being urged distally during engagement of plunger assembly 200 and end effector assembly 320, thus facilitating the engagement of plunger assembly 200 and end effector assembly 320 by retaining push bar 322 in a substantially fixed position, and also inhibiting accidental deployment of end effector assembly 320. Thus, upon engagement of plunger assembly 200 and end effector assembly 320, plunger assembly 200 is moved from the disengaged position to the proximal use position, but is inhibited from being transitioned to the distal use position (which effects deployment of end effector assembly 320) due to the engagement of lock tab 400 about distal end 301 of cartridge assembly 300.

Figure 12:
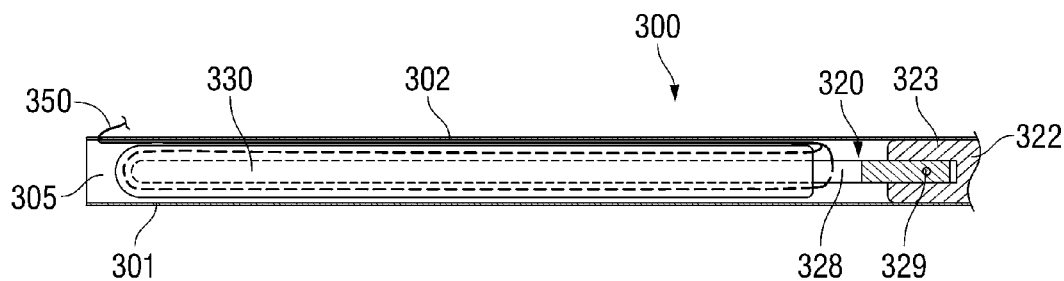
FIG. 12 is a longitudinal, cross-sectional view of a distal end of the cartridge assembly with an end effector assembly in the retracted position.
Figure 13A:
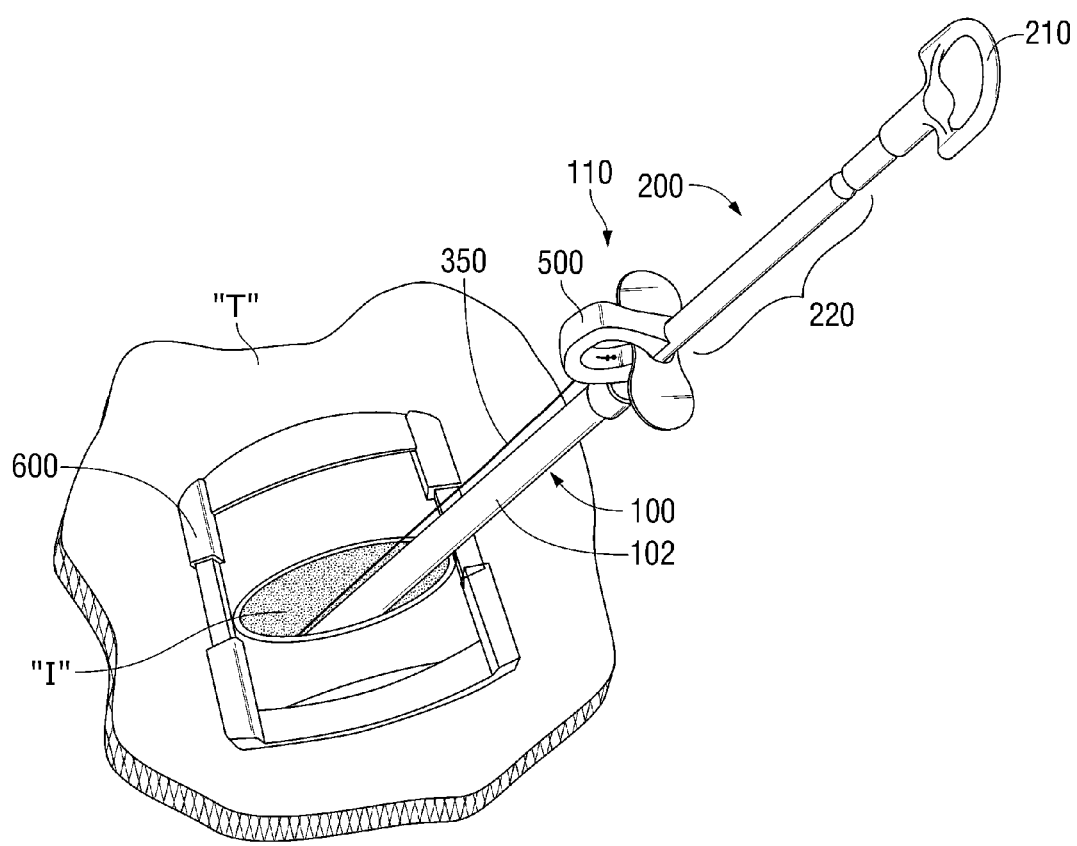
FIG. 13A is a perspective view of the surgical retrieval apparatus being inserted through an access port positioned within an opening in tissue.
Figure 13B:
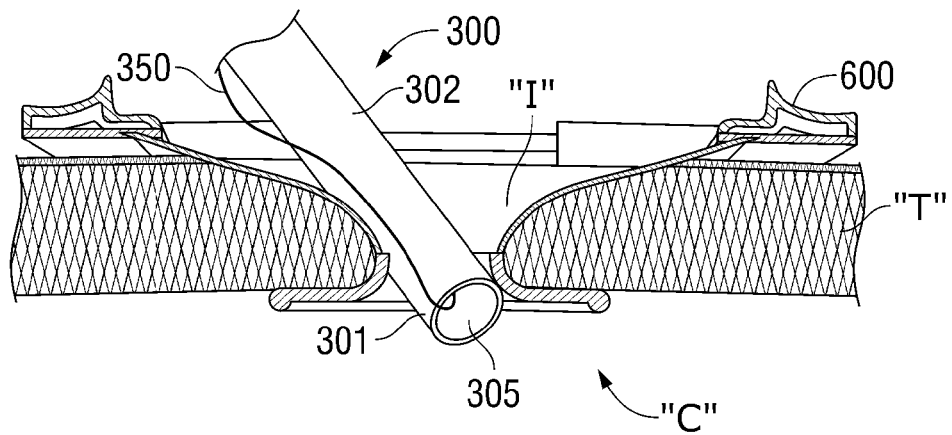
FIG. 13B is a cross-sectional view of the distal end of the cartridge assembly being inserted through the access port of FIG. 13A and into an internal body cavity, wherein the end effector assembly is in the retracted position.

Turning now to FIGS. 11-12, with cartridge assembly 300 engaged with tube assembly 100 and with plunger assembly 200 engaged with end effector assembly 320 in the proximal use position, surgical retrieval apparatus 10 is fully assembled for use. Once this fully assembled condition has been achieved, and in preparation for use, lock tab 400 is removed from distal end 301 of tubular housing 302 cartridge assembly 300, i.e., central finger 411 is withdrawn from lock slot 314, and is discarded. Removal of lock tab 400 permits selective movement of plunger assembly 200 between the proximal and distal use positions to move end effector assembly 320 between the refracted and deployed positions, i.e., removal of lock tab 400 "unlocks" end effector assembly 320. It is noted that, once lock tab 400 has been removed, end effector assembly 320 still remains disposed in the retracted position and is inhibited from inadvertent movement due to the frictional engagement of O-rings 326a, 326b disposed about push bar 322 (FIG. 5A) with the internal surface of tubular housing 302.

Pull ring 500 is also removed from distal end 301 of tubular housing 302 of cartridge assembly 300 in preparation for use. Pull ring 500, which is initially disposed towards distal end 301 of tubular housing 302, is moved from the initial position to the use position, wherein pull ring 400 is disposed about grasping portion 110 of tube assembly 100. More specifically, pull ring 500 is moved from the initial position to the use position, wherein pull ring 500 is positioned such that distal cuff 520 of pull ring 500 is disposed about proximal segment 118 of elongated tubular member 102 of tube assembly 100, i.e., between annular cuff 114 and grasping portion 110 of tube assembly 100, while proximal contact member 540 of pull ring 500 extends proximally beyond tube assembly 100 to rest atop the portion of shaft 220 of plunger assembly 200 adjacent to grasping portion 110 of tube assembly 100. The positioning of distal cuff 520 of pull ring 500 between annular cuff 114 and grasping portion 110 of elongated tubular member 102 of tube assembly 100 maintains pull ring 500 in substantially fixed longitudinal position relative to elongated tubular member 102.

With continued reference to FIGS. 11-12, although second end 354 of cinch cord 350 is pulled proximally due to the movement of pull ring 500 from distal end 301 of tubular housing 302 of cartridge assembly 300 to proximal end 106 of elongated tubular member 102 of tube assembly 100 (due to the engagement of second end 354 of cinch cord 350 with pull ring 500), cinch cord 350 is provided with sufficient slack such that specimen retrieval bag 330 is not cinched closed during this movement of pull ring 500. Rather, in this position, cinch cord 350, in a substantially un-tensioned state, simply extends distally from lumen 104 of tubular housing 302 of cartridge assembly 300, through cord aperture 318 of cord slot 316 defined within tubular housing 302, and proximally along the outer periphery of tubular housing 302 and elongated tubular member 102, ultimately engaging pull ring 500. Further, as shown in FIG. 12, at this point, end effector assembly 320 remains disposed within lumen 305 of tubular housing 302 of cartridge assembly 300, i.e., end effector assembly 320 remains in the retracted position, wherein arms 328 are disposed in close proximity to one another and wherein specimen retrieval bag 330 remains rolled or folded within lumen 305.

Referring to FIGS. 13A-13B, with surgical retrieval apparatus 10 fully assembled, plunger assembly 200 engaged with end effector assembly 320 in the proximal use position, lock tab 400 removed from cartridge assembly 300, and pull ring 500 moved to the use position, surgical retrieval device 10 is ready for use. In use, surgical retrieval device 10 is initially inserted, lead by distal end 301 of tubular housing 302 of cartridge assembly 300, into an internal surgical site, or body cavity "C," e.g., surgical retrieval device 10 is inserted through a surgical access portal 600 positioned within an opening or incision "I" in tissue "T," although surgical retrieval apparatus 10 may alternatively be directly inserted through the opening or incision "I," or may be used in conjunction with any other suitable access portal (not shown). As can be appreciated, in this initial position, with end effector assembly 320 retracted within cartridge assembly 300, surgical retrieval apparatus 10 defines a reduced diameter to facilitate passage of cartridge assembly 300 and tube assembly 100 through access portal 600, the opening or incision "I" in tissue "T," and into the internal surgical site "C." Cinch cord 350, which extends proximally along the outer surface of cartridge assembly 300 and tube assembly 100 to engage pull ring 500, is disposed through cord aperture 318 of cord slot 316 (FIG. 15) at distal end 301 of tubular housing 302 of cartridge assembly 300 so as to inhibit catching or otherwise interfering with the insertion of surgical retrieval apparatus 10 into the internal surgical site "C."

Figure 13C:
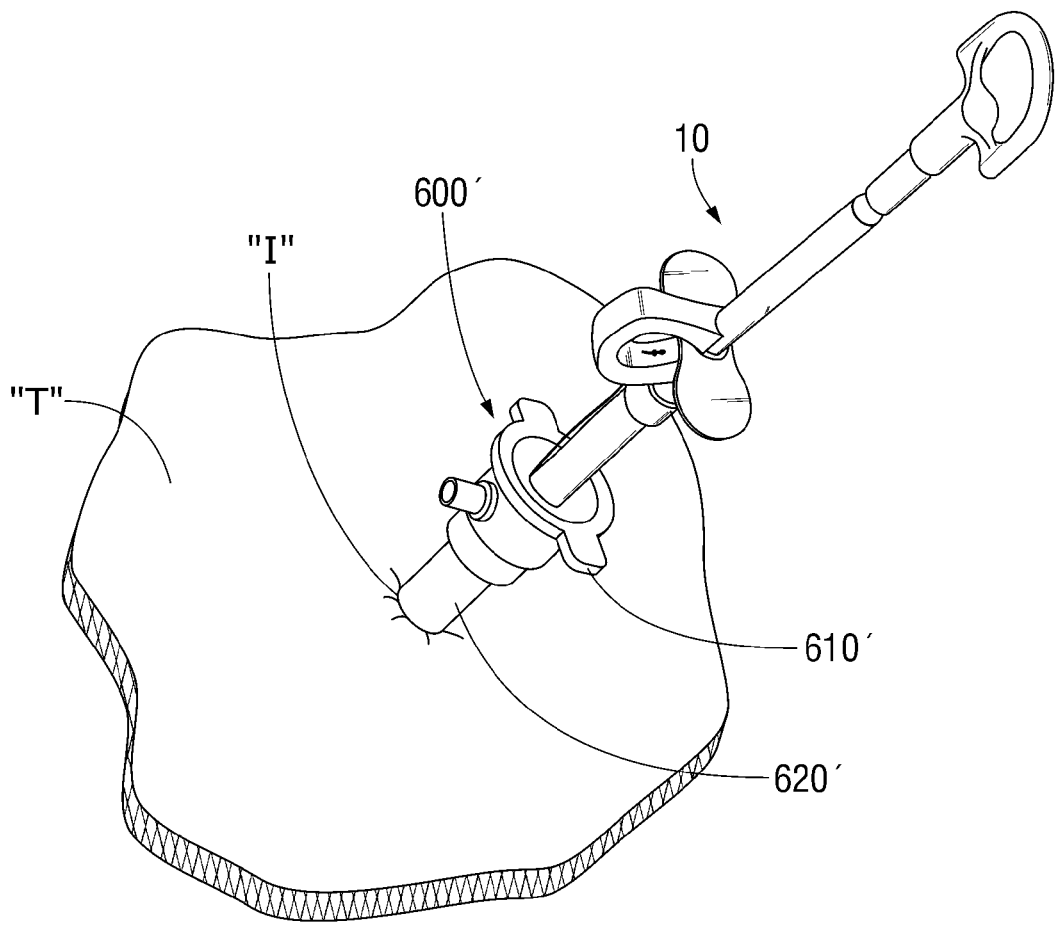
FIG. 13C is a perspective view of the surgical retrieval apparatus being inserted through a cannula positioned within an opening in tissue.
Figure 13D:
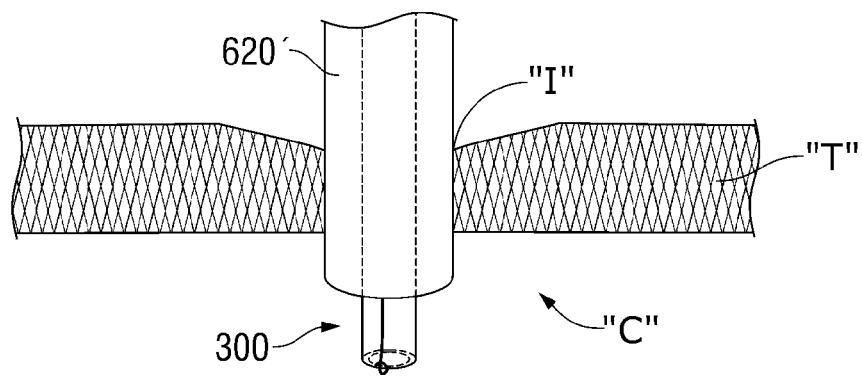
FIG. 13D is a cross-sectional view of the distal end of the cartridge assembly being inserted through the cannula of FIG. 13C and into an internal body cavity, wherein the end effector assembly is in the retracted position.

Referring momentarily to FIGS. 13C-13D, surgical retrieval apparatus 10 is shown inserted through a cannula 600' disposed within the incision "I" in tissue "T." Although one embodiment of a cannula 600' is shown in FIGS. 13C-13C, it is envisioned that other suitable cannulas and/or access portals may also be provided for use with surgical retrieval apparatus 10. Cannula 600' generally includes a housing 610' and an outer sleeve 620' that is configured to permit passage of surgical retrieval apparatus 10 therethrough to facilitate the positioning of cartridge assembly 300 within the internal surgical site "C." Cannula 600' may be used in conjunction with a trocar (not shown) to pierce tissue and/or provide access to the internal surgical site "C," with the trocar (not shown) subsequently being removed to permit insertion of surgical retrieval apparatus 10 through cannula 600'. The use of surgical retrieval apparatus 10 in conjunction with cannula 600' is substantially similar to the use of surgical retrieval apparatus 10 in conjunction with access portal 600 and, thus, will not be repeated herein to avoid unnecessary repetition.

Figure 14A:
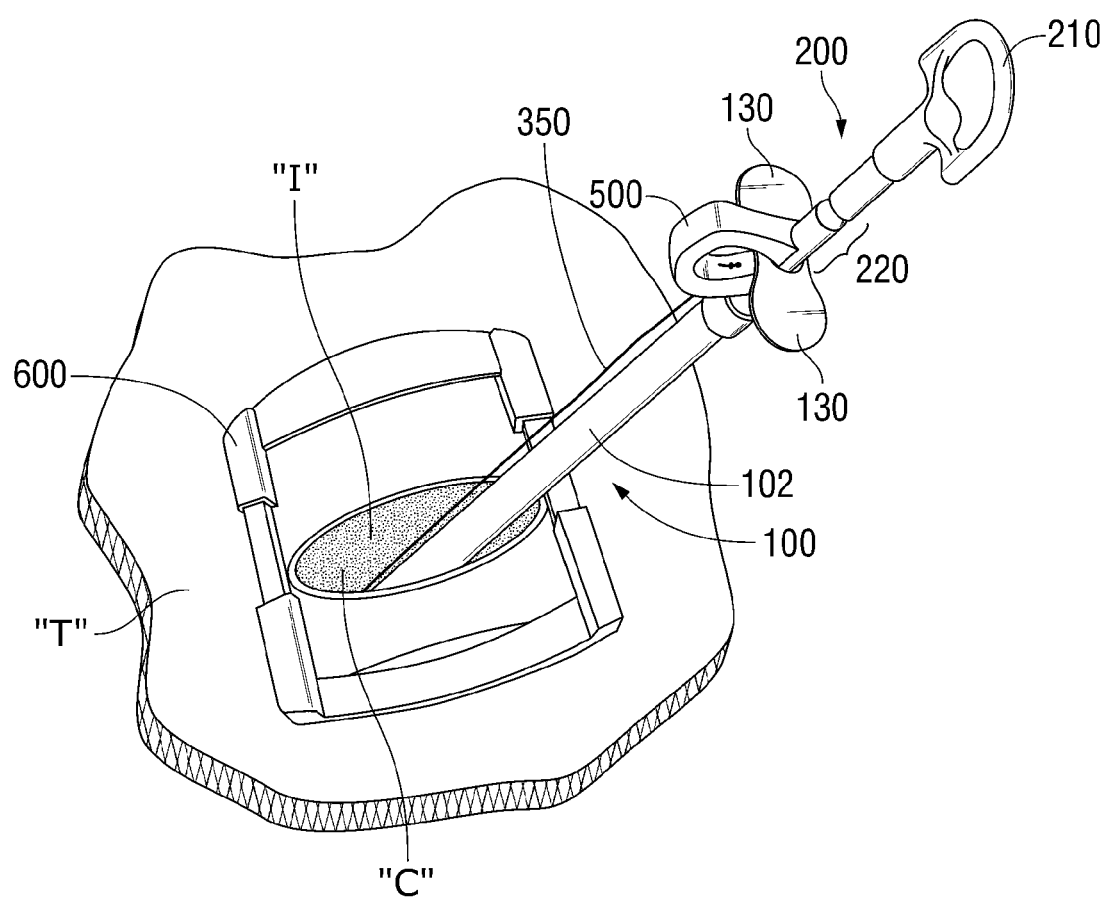
FIG. 14A is a perspective view of the surgical retrieval apparatus inserted through the access port positioned within the opening in tissue with the plunger assembly in a distal position.
Figure 14B:
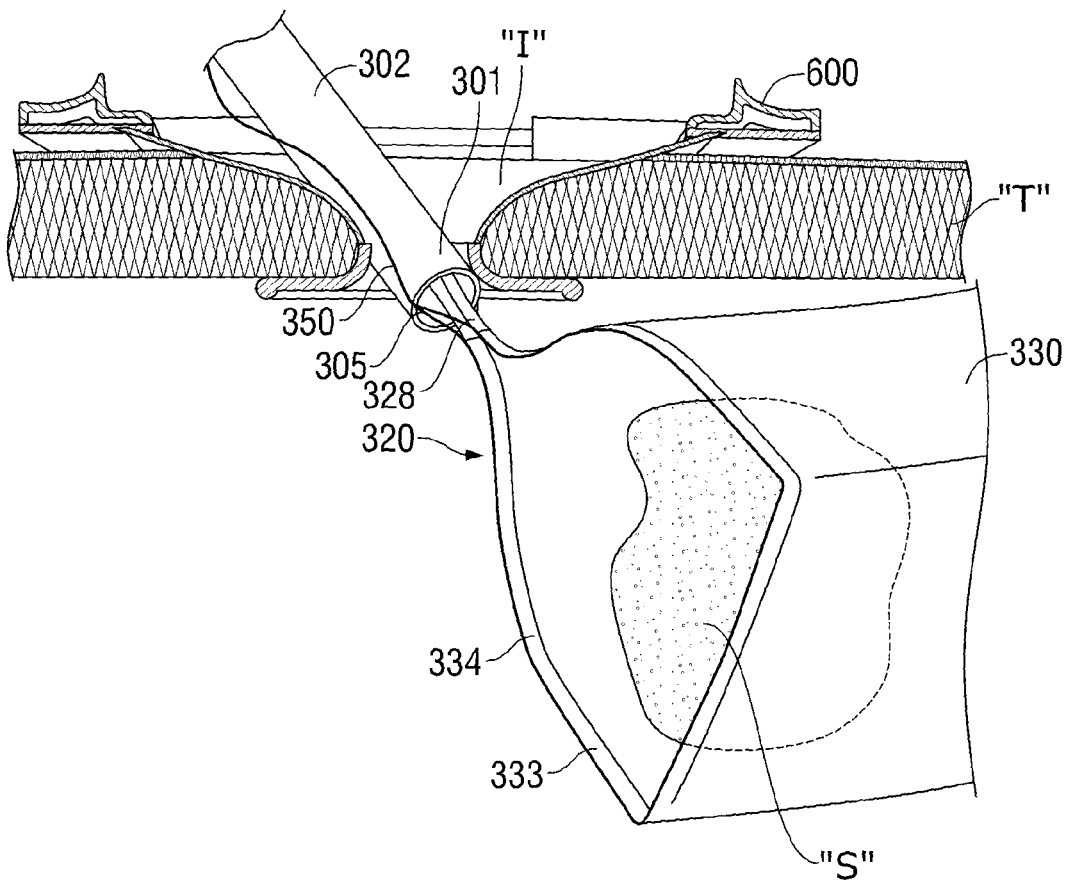
FIG. 14B is cross-sectional view of the distal end of the cartridge assembly inserted through the access port and into the internal body cavity, wherein the end effector assembly is in a deployed position to deploy a specimen retrieval bag.
Figure 15:
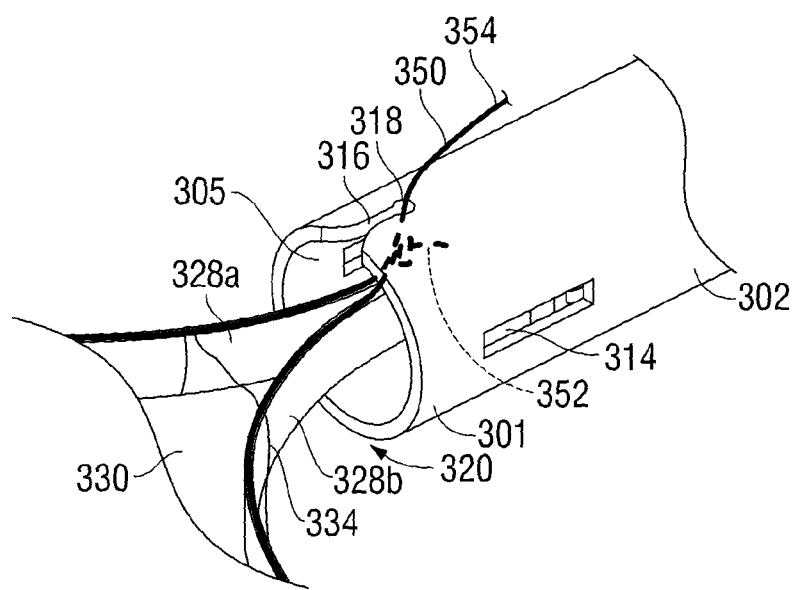
FIG. 15 is an enlarged, perspective view of the distal end of the cartridge assembly with the end effector assembly in the deployed position.

With reference to FIGS. 14A-14B and 15, once surgical retrieval apparatus 10 has been inserted into the internal surgical site "C" and manipulated into position, plunger assembly 200 may be translated distally relative to tube assembly 100 from the proximal use position to the distal use position such that shaft 220 of plunger assembly 200 is advanced distally through lumen 104 of elongated tubular member 102 and into lumen 305 of tubular housing 302. In order to move plunger assembly 200 relative to tube assembly 100, the user grasps handle 210 of plunger assembly 200 and translated plunger assembly 200 distally while also grasping flanges 130 of grasping portion 110 of tube assembly 100 to maintain tube assembly 100 and cartridge assembly 300 in substantially stationary position. As plunger assembly 200 is advanced distally relative to and through tube assembly 100 and cartridge assembly 300, proximal contact 540 of pull ring 500 is translated along the outer peripheral surface of proximal segment 226 of shaft 220 until proximal contact 540 of pull ring 500 abuts second step 234 formed along shaft 220 between proximal segment 226 and neck 230 thereof (see FIG. 19A). The abutment of proximal contact 540 and second step 234 inhibits further distal translation of plunger assembly 200 and defines the distal use position of plunger assembly 200 (see FIG. 19A).

This position, as detailed below, corresponds to the deployed position of end effector assembly 320. Thus, second step 234 of shaft 220 helps ensure proper and fully deployment of end effector assembly 320 by inhibiting over-translation of plunger assembly 200 beyond the distal use position (see FIG. 19A).

As mentioned above, due to the engagement of annular protrusion 1328 of push bar 322 of end effector assembly 320 and annular recess 242 of distal head portion 240 of shaft 220 of plunger assembly 200 (see FIG. 9B), distal translation of plunger assembly 200 from the proximal use position to the distal use position effects corresponding distal translation of push bar 322 and, thus, end effector assembly 320, relative to cartridge assembly 300. More specifically, as plunger assembly 200 is translated distally through tube assembly 100 and cartridge assembly 300 from the proximal use position to the distal use position, end effector assembly 320 is urged from the retracted position to the deployed position to deploy arms 328 and specimen retrieval bag 330 from tubular housing 302 of cartridge assembly 300. As arms 328 of end effector assembly 320 emerge from tubular housing 302 of cartridge assembly 300, specimen retrieval bag 330 is deployed, or unrolled, to the open condition, as shown in FIG. 14B. That is, the bias of arms 328 towards the spaced-apart, curvate configuration and the bias of support member 340 (FIG. 5B) disposed within specimen retrieval bag 330 facilitates the deployment of specimen retrieval bag 330 to the open condition as end effector assembly 320 emerges from cartridge assembly 300.

With end effector assembly 320 of surgical retrieval apparatus 10 disposed within the internal surgical site "C" in the deployed condition such that specimen retrieval bag 330 is disposed in the open condition, the specimen of tissue "S" may be moved into specimen retrieval bag 330, e.g., via manipulation of surgical retrieval apparatus 10 and/or via use of additional surgical instrumentation (e.g., a surgical grasper (not shown)). As shown in FIG. 15, at this point, cinch cord 350 remains disposed in a substantially un-tensioned position such that specimen retrieval bag 330 is retained in an open condition under the bias of arms 328 of end effector assembly 320. Once the specimen of tissue "S" to be retrieved is disposed within specimen retrieval bag 330, specimen retrieval bag 330 may be cinched closed and subsequently removed from the internal surgical site "C."

Figure 16:
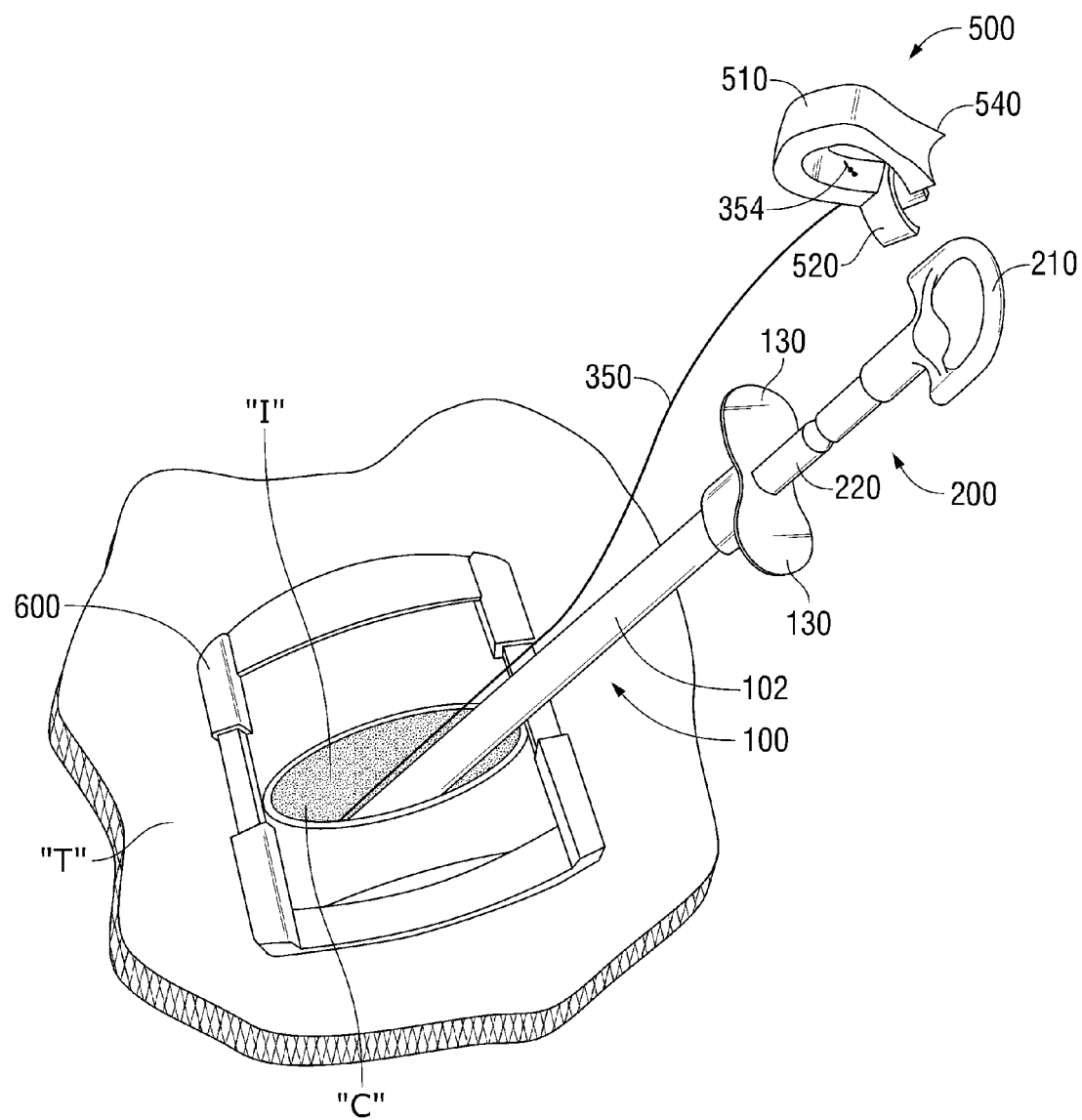
FIG. 16 is a perspective view of the surgical retrieval apparatus inserted through the access port positioned within the opening in tissue with the pull-ring disengaged from the tube assembly.
Figure 17:
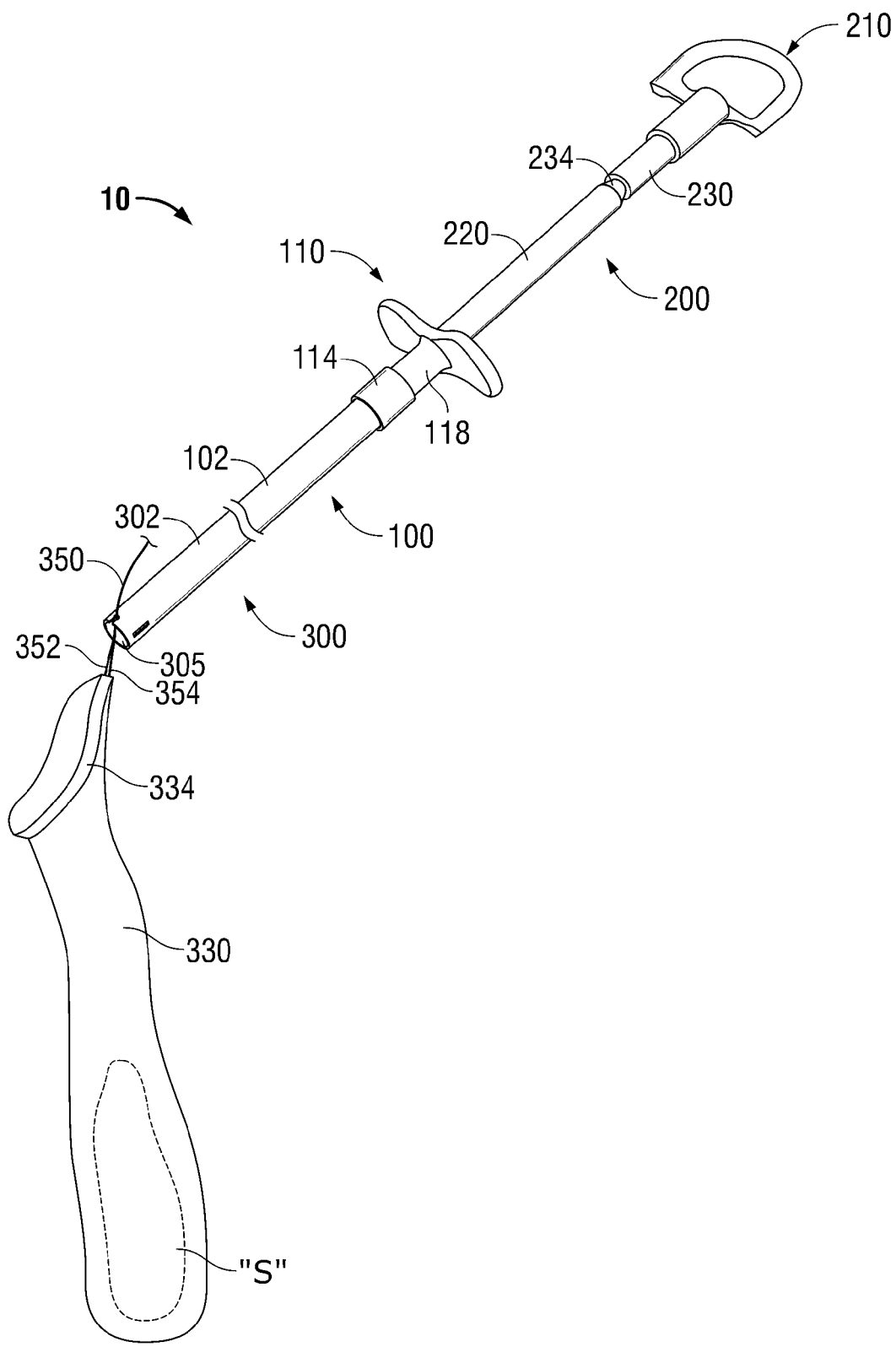
FIG. 17 is a perspective view of the surgical retrieval apparatus with the end effector assembly in the retracted position and the specimen retrieval bag cinched closed.

With reference to FIGS. 15-18, in order to cinch closed specimen retrieval bag 330 to secure the specimen of tissue "S" therein, pull ring 500 is disengaged from tube assembly 100 and is translated proximally relative to surgical retrieval apparatus 10, as best shown in FIG. 16. Cinch cord 350, as mentioned above, extends through loop 334 formed at open end 333 of specimen retrieval bag 330, with first end 352 of cinch cord 350 looped around second end 354 of cinch cord 350 on a distal side of cord slot 316 and with second end 354 of cinch cord 350 extending proximally through cord aperture 318 of cord slot 316 to engage pull ring 500. Thus, as pull ring 500 is translated proximally, second end 354 of cinch cord 350 is likewise translated proximally to increasingly tension the portion of cinch cord 350 disposed through loop 334 of specimen retrieval bag 330, thereby constricting, or cinching closed open end 333 of specimen retrieval bag 330. Further, since first end 352 of cinch cord 350 is looped about second end 354 of cinch cord 350 on a distal side of cord slot 316, the looped first end 352 of cinch cord 350 is inhibited from passing proximally through cord aperture 318 of cord slot 316. As such, proximal translation of pull ring 500 does not effect translation of specimen retrieval bag 330, but, rather, effects only tensioning of cinch cord 350 about open end 333 of specimen retrieval bag 330 to cinch closed specimen retrieval bag 330. Further, the looping of first end 352 of cinch cord 350 about second end 354 thereof may also be configured to inhibit un-tensioning of cinch cord 350, thereby maintaining specimen retrieval bag 330 in the cinched-closed condition without requiring the user to maintain the tension on second end 354 of cinch cord 350.

With specimen retrieval bag 330 cinched closed with the specimen of tissue "S" therein, end effector assembly 320 may be returned to the retracted position such that surgical retrieval device 10 and specimen retrieval bag 330 may be removed from the internal surgical site "C." In order to return surgical retrieval device 10 to the retracted position, the user once again grasps handle 210 of plunger assembly 200 and flanges 130 of grasping portion 110 of tube assembly 100 and translates plunger assembly 200 proximally relative to tube assembly 100. Due to the engagement of annular protrusion 1328 of push bar 322 of end effector assembly 320 and annular recess 242 of distal head portion 240 of shaft 220 (see FIG. 9B), proximal translation of plunger assembly 200 from the distal use position back to the proximal use position effects corresponding proximal translation of push bar 322 to translate arms 328 of end effector assembly 320 back into lumen 305 of tubular housing 302 of cartridge assembly 300. With cinch cord 350 disposed through cord aperture 318 of cord slot 316 and cinched about specimen retrieval bag 330, translation of arms 328 of end effector assembly 320 back into lumen 305 of tubular housing 302 of cartridge assembly 300 effects withdrawal of arms 328 from loop 334 of specimen retrieval bag 330 such that specimen retrieval bag 330 remains disposed within the internal surgical site "C," distally of cartridge assembly 300, despite the retraction of end effector assembly 320 back into cartridge assembly 300. Alternatively, with reference also to FIG. 5D, in embodiments where specimen retrieval bag 330' is used, upon proximal translation of plunger assembly 200 from the distal use position back to the proximal use position, arms 328 and upper sleeve 334' of specimen retrieval bag 330' are pulled back into lumen 305 of tubular housing 302 of cartridge assembly 300, while the remainder of specimen retrieval bag 330', which was separated from upper sleeve 334' along scoring 341' of intermediate portion 339' during closure of specimen retrieval bag 330', remains disposed within the internal surgical site "C," distally of cartridge assembly 300.

Figure 18:
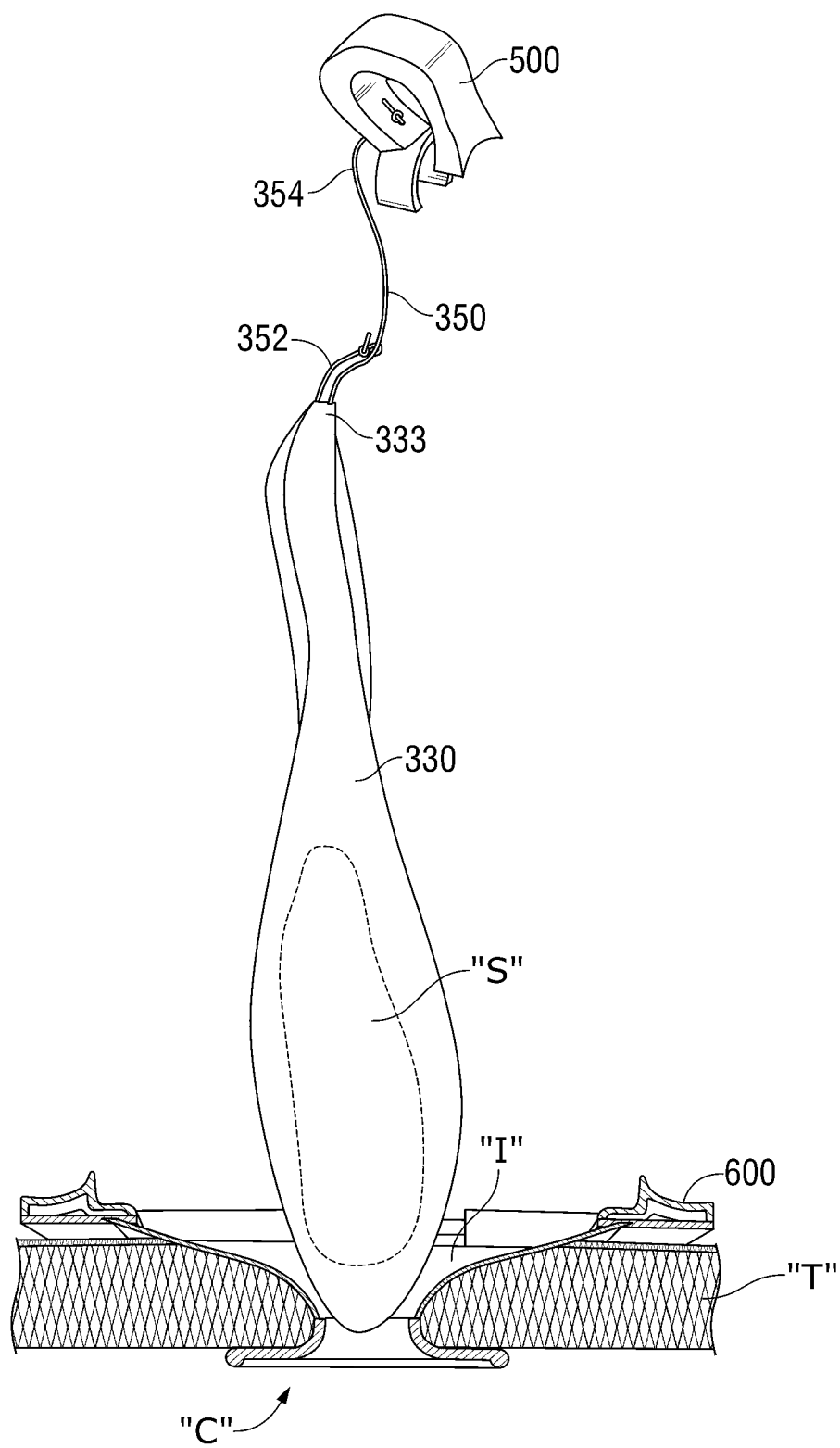
FIG. 18 is a cross-sectional view of the specimen retrieval bag being removed from the internal body cavity through the access port.

Once end effector assembly 320 has been retracted back within cartridge assembly 300, surgical retrieval apparatus 10, once again defining a reduced diameter, may be withdrawn from the internal surgical site "C" through access portal 600 (or cannula 600' (FIGS. 13C-13D) disposed within the opening or incision "I" in tissue "T." Thereafter, as shown in FIG. 18, specimen retrieval bag 330, lead by pull ring 500 and cinch cord 350, may likewise be withdrawn from the internal surgical site "C" through access portal 600.

At the completion of the tissue specimen "S" removal procedure, surgical retrieval apparatus 10 is disassembled such that the reusable components, e.g., tube assembly 100 and plunger assembly 200 may be sterilized for reuse, while the first set of disposable components, e.g., cartridge assembly 300, lock tab 400, and pull ring 500, may be discarded. As described above, specimen retrieval bag 330, lock tab 400, and pull ring 500 are disengaged from the remainder of surgical retrieval apparatus 10 during use, and, thus, may be disposed of at the completion of the procedure. Cartridge assembly 300, on the other hand, remains engaged with tube assembly 100 throughout use of surgical retrieval apparatus 10 and, thus, is required to be disengaged from tube assembly 100 at the completion of the procedure.

Figure 19B:
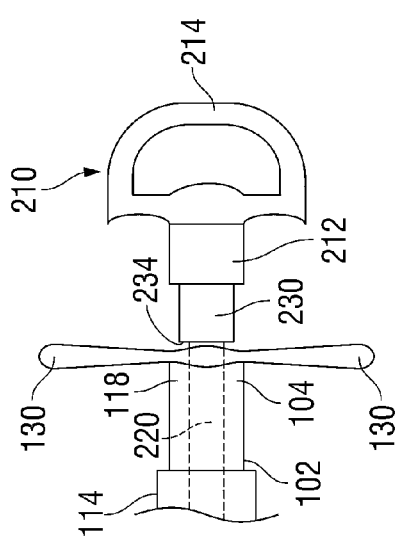
FIG. 19B is a side view of the proximal end of the tube assembly with the plunger assembly inserted further therethrough to an eject position.

Turning now to FIGS. 19A-21, in order to disengage cartridge assembly 300 from tube assembly 100 and to disengage plunger assembly 200 from end effector assembly 320 of cartridge assembly 300, plunger assembly 200 is translated from the proximal use position (FIG. 11), past the distal use position (FIG. 19A), to the eject position (FIG. 19B). That is, with pull ring 500 no longer disposed in the use position about grasping portion 110 of tube assembly 100 (see FIG. 19A), distal translation of plunger assembly 200 beyond the distal use position is no longer inhibited by the abutment of proximal contact 540 of pull ring 500 and second step 234 of shaft 220. As such, plunger assembly 200 may be translated beyond the distal use position to the eject position, as shown in FIG. 19B.

Figure 20A:
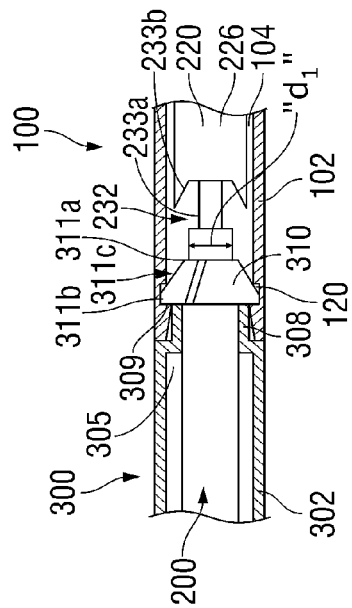
FIG. 20A is a longitudinal, cross-sectional view of the cartridge assembly and the tube assembly in an engaged position.
Figure 20B:
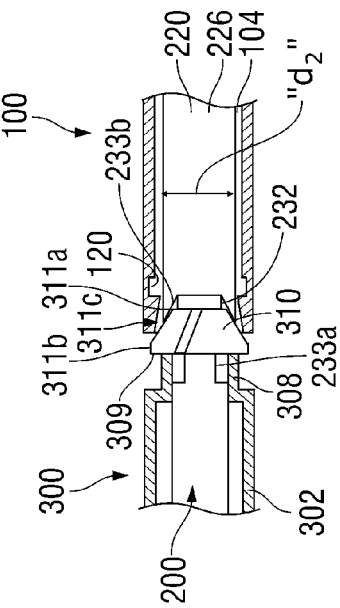
FIG. 20B is a longitudinal, cross-sectional view of the cartridge assembly and the tube assembly showing the cartridge assembly being separated from the tube assembly.
Figure 21:
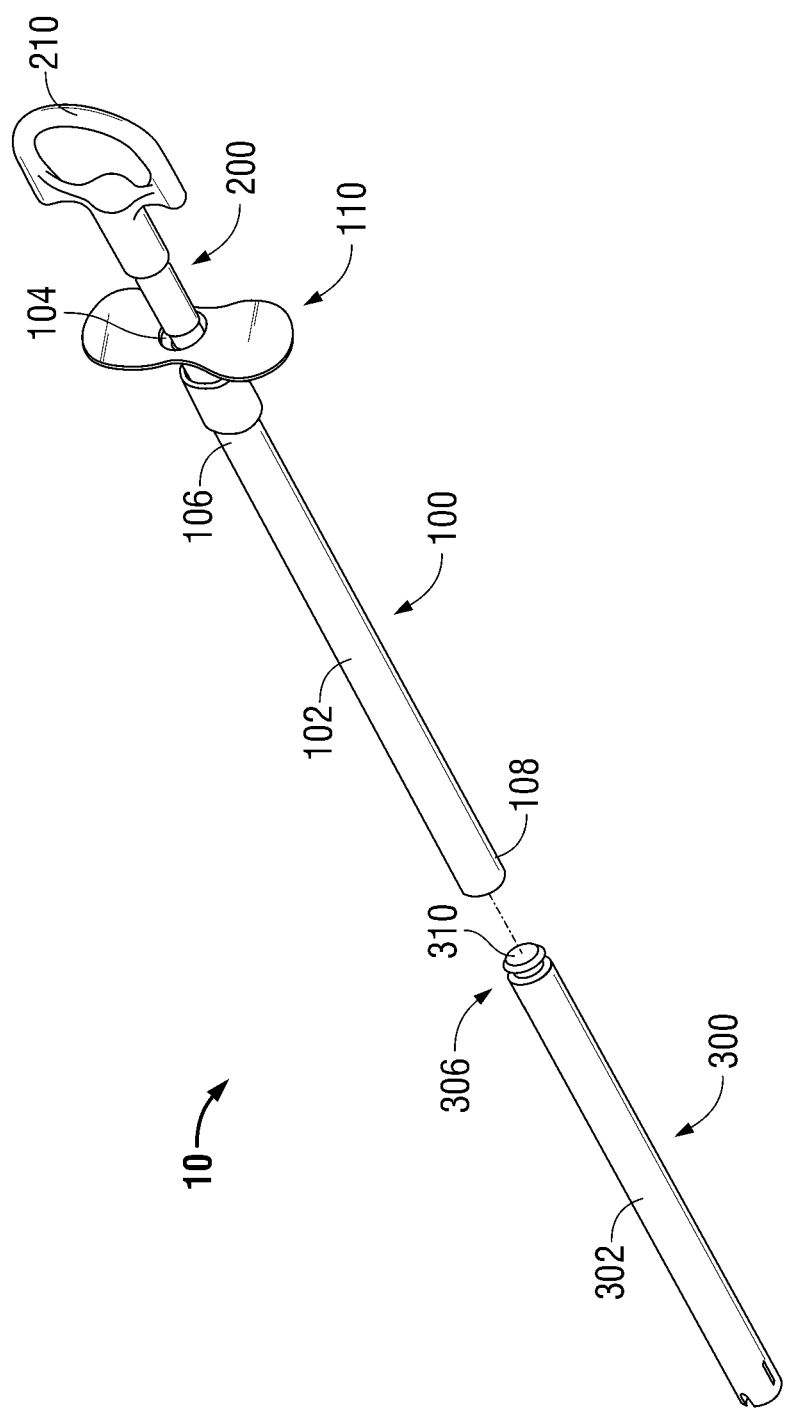
FIG. 21 is a perspective view of the surgical retrieval apparatus wherein the cartridge assembly has been separated from the tube assembly and the plunger assembly.

Referring to FIGS. 20A-20B and 21, as plunger assembly 200 is translated distally from the proximal use position towards the eject position, distal segment 222 of shaft 220 is translated distally through lumen 305 of tubular housing 302 of cartridge assembly 300 and proximal segment 226 of shaft 220 is translated distally through lumen 104 of elongated tubular member 102 of tube assembly 100 towards cap 306 of tubular housing 302 of cartridge assembly 300. Distal segment 222 of shaft 220, as mentioned above, defines a diameter "$d_1$" that is sufficiently small so as to permit passage of distal segment 222 of shaft 220 through lumen 305 of tubular housing 300. Proximal segment 226 of shaft 220, on the other hand, defines a relatively larger diameter "$d_2$" that is larger than the diameter of lumen 305 so to inhibit passage of proximal segment 226 into lumen 305 of tubular housing 302. Accordingly, as plunger assembly 200 is translated further distally towards the eject position, angled surface 233b defined by recess 233a and first step 232, eventually abuts proximal end 311a of head 310 of cap 306. In other words, first step 232, due to the relatively larger diameter "$d_2$" of proximal segment 226 of shaft 220 as compared to diameter "$d_1$" of distal segment 222 of shaft 220, is inhibited from passing through lumen 305 and, instead, abuts proximal end 311a of head 310 of cap 306. Upon further distal translation of plunger assembly 200 towards the eject position, angled surface 233 of recess 233a and first step 232 is urged distally into proximal end 311a of head 310 of cap 306 such that head 310, facilitated by relief slots 312, is compressed to a reduced diameter. The compression of head 310 of cap 306 disengages lip 309 and distal end 311b of head 310 from within annular recess 120 defined within elongated tubular member 102 and, thereafter, urges head 310 distally, such that cartridge assembly 300 is disengaged, or ejected from tube assembly 100. Ejection of cartridge assembly 300 may be confirmed by an audible and/or tactile "snap" or "click," indicating that lip 309 and distal end 311b of head 310 have been disengaged from within annular recess 120 of elongated tubular member 102.

Once cartridge assembly 300 has been disengaged from tube assembly 100, as described above, the user may grasp handle 210 of plunger assembly 200 and tubular housing 302 of cartridge assembly 300 and translate plunger assembly 200 and cartridge assembly 300 apart from one another to disengage annular protrusion 1328 and annular recess 242 from one another (FIGS. 9A-9B). More specifically, with additional reference to FIGS. 9A and 9B, upon moving plunger assembly 200 and cartridge assembly 300 apart from one another, distal head portion 240 of shaft 220 is compressed and/or hollow proximal end 327 of push bar 322 is expanded such that distal head portion 240 is permitted to pass proximally back through annular protrusion 1328, thereby disengaging annular protrusion 1328 from within annular recess 242. With annular protrusion 1328 and annular recess 242 no longer engaged with one another, shaft 220 of plunger assembly 200 may be withdrawn from hollow proximal end 327 of push bar 322 of end effector assembly 320. Thereafter, cartridge assembly 300, including end effector assembly 320, may be discarded. Plunger assembly 200 may then be removed from tube assembly 100 such that plunger assembly 200 and tube assembly 100 may be sterilized for reuse.

As can be appreciated, adequate sterilization of tube assembly 100 and plunger assembly 200 is readily achieved due to the minimal complex features of these components. The construction of tube assembly 100 and plunger assembly 200 from a strong, durable material, e.g., stainless steel, inhibits wear and fatigue of these components throughout a plurality of uses. Cartridge assembly 300, lock tab 400, and pull ring 500, on the other hand, are disposable components that are replaced with a new, second set of disposable components for the next use. Accordingly, these components need not be configured to withstand sterilization or a plurality of uses. Further, surgical retrieval apparatus 10 is advantageous in that substantial disassembly and/or complex sterilization procedures are avoided without requiring an entirely new instrument for each use.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical retrieval apparatus, comprising:
  a tube having a first lumen extending longitudinally therethrough, the tube defining a first mechanical engagement feature positioned towards a distal end thereof and radially disposed about the first lumen such that the first lumen extends longitudinally through the first mechanical engagement feature;
  a cartridge assembly including a housing having a second lumen and an end effector assembly operably disposed within the second lumen, the housing defining a second mechanical engagement feature positioned towards a proximal end thereof and radially disposed about the second lumen such that the second lumen extends longitudinally through the second mechanical engagement feature, the first and second mechanical engagement features configured to releasably engage each other to directly mechanically engage the housing with the tube, the end effector assembly including a specimen retrieval bag releasably coupled thereto;
  a plunger configured for insertion through the first lumen of the tube, the first mechanical engagement feature, the second mechanical engagement feature, and at least partially into the second lumen of the housing to releasably engage the end effector assembly within the second lumen of the housing when the housing is engaged with the tube, wherein, when the plunger and the end effector assembly are engaged with one another, the plunger is movable through the first and second lumens and relative to the tube and the housing between a more proximal position, wherein the end effector assembly and specimen retrieval bag are retracted within the second lumen of the housing, and a more distal position, wherein the end effector assembly extends distally from the housing to deploy the specimen retrieval bag; and a lock tab releasably engagable about a portion of the exterior of the housing of the cartridge assembly, the lock tab including a finger configured to extend through a slot defined within the housing and at least partially into the second lumen when the lock tab is engaged about the portion of the exterior of the housing, such that the finger blocks distal movement of the end effector assembly through the second lumen of the housing.

2. The surgical retrieval apparatus according to claim 1, wherein the first and second mechanical engagement features are configured for snap-fit engagement with one another.

3. The surgical retrieval apparatus according to claim 2, wherein an audible feedback signal is produced upon snap-fit engagement of the first and second mechanical engagement features with one another.

4. The surgical retrieval apparatus according to claim 1, wherein the plunger and the end effector assembly are configured for snap-fit engagement with one another.

5. The surgical retrieval apparatus according to claim 4, wherein an audible feedback signal is produced upon snap-fit engagement of the plunger and the end effector assembly with one another.

6. The surgical retrieval apparatus according to claim 1, wherein the plunger is further movable relative to the tube and the housing to an eject position to disengage the first and second mechanical engagement features from one another.

7. The surgical retrieval apparatus according to claim 1, further comprising a cinch cord coupled to an open end of the specimen retrieval bag, the cinch cord selectively tensionable to cinch closed the specimen retrieval bag.

8. The surgical retrieval apparatus according to claim 7, further comprising a cord slot defined within the housing, the cord slot configured to receive the cinch cord therethrough to facilitate closing of the specimen retrieval bag upon tensioning of the cinch cord.

9. The surgical retrieval apparatus according to claim 7, further comprising a pull ring coupled to the cinch cord, the pull ring selectively movable relative to the end effector assembly to cinch closed the specimen retrieval bag.

10. The surgical retrieval apparatus according to claim 9, wherein the pull ring is movable from an initial position, wherein the pull ring is disposed about the housing, to a use position, wherein the pull ring is disposed about the tube.

11. The surgical retrieval apparatus according to claim 10, wherein the pull ring is removable from the use position and is movable proximally therefrom to cinch closed the specimen retrieval bag.

12. The surgical retrieval apparatus according to claim 7, wherein the specimen retrieval bag includes a perforated section adjacent the open end thereof, the specimen retrieval bag configured to tear along the perforated section as the specimen retrieval bag is cinched closed to disengage the specimen retrieval bag from the end effector assembly.

13. The surgical retrieval apparatus according to claim 1, wherein the tube and the plunger are formed as reusable components and wherein the cartridge assembly is formed as a disposable component.

14. A surgical kit, comprising:
a reusable tube defining a first mechanical engagement feature positioned towards a distal end thereof, the reusable tube having a first lumen extending longitudinally through the reusable tube and the first mechanical engagement feature;
a reusable plunger; and
a plurality of disposable cartridge assemblies, each cartridge assembly including:
a housing defining a second mechanical engagement feature positioned towards a proximal end thereof, the housing having a second lumen extending longitudinally through the housing and the second mechanical engagement feature, the first mechanical engagement feature of the reusable tube configured to engage the second mechanical engagement feature of the housing to releasably engage the reusable tube with the housing;
an end effector assembly operably disposed within the second lumen of the housing, the end effector assembly including a specimen retrieval bag that is deployable from the housing upon movement of the end effector assembly from a retracted position to an extended position, the end effector assembly releasably engagable with the reusable plunger within the second lumen of the housing upon insertion of the reusable plunger through the first lumen of the reusable tube and at least partially into the second lumen of the housing, wherein, with the reusable plunger engaged with the end effector assembly, movement of the reusable plunger between a more proximal position and a more distal position moves the end effector assembly between the retracted position and the extended position; and
a lock tab releasably engagable about a portion of the exterior of the housing of the cartridge assembly, the lock tab including a finger configured to extend through a slot defined within the housing and at least partially into the second lumen when the lock tab is engaged about the portion of the exterior of the housing, such that the finger blocks distal movement of the end effector assembly through the second lumen of the housing.

15. The surgical kit according to claim 14, wherein the reusable plunger is further movable from the more distal position to an eject position to disengage the first and second mechanical engagement features from one another.

16. The surgical kit according to claim 14, wherein the reusable tube and the reusable plunger are each formed from stainless steel to facilitate sterilization and reuse of the reusable tube and the reusable plunger.

17. The surgical kit according to claim 14, wherein feedback is provided upon engagement of the first and second mechanical engagement features with one another.

18. The surgical kit according to claim 14, wherein feedback is provided upon engagement of the reusable plunger and the end effector assembly of each of the plurality of disposable cartridge assemblies with one another.

* * * * *